United States Patent
Green, Jr. et al.

(10) Patent No.: US 7,697,971 B1
(45) Date of Patent: *Apr. 13, 2010

(54) POSITIONING SYSTEM FOR AN MRI

(75) Inventors: Charles A. Green, Jr., Holbrook, NY (US); Mark Gelbien, Levittown, NY (US); William H. Wahl, Smithtown, NY (US); Raymond V. Damadian, Woodbury, NY (US)

(73) Assignee: Fonar Corporation, Melville, NY (US)

( * ) Notice: Subject to any disclaimer, the term of this patent is extended or adjusted under 35 U.S.C. 154(b) by 1138 days.

This patent is subject to a terminal disclaimer.

(21) Appl. No.: 09/918,369

(22) Filed: Jul. 30, 2001

Related U.S. Application Data

(63) Continuation-in-part of application No. 09/718,946, filed on Nov. 22, 2000, now Pat. No. 6,677,753.

(60) Provisional application No. 60/222,098, filed on Jul. 28, 2000, provisional application No. 60/252,837, filed on Nov. 22, 2000.

(51) Int. Cl.
*A61B 5/05* (2006.01)

(52) U.S. Cl. .......................... 600/415; 5/601; 600/410; 324/307

(58) Field of Classification Search .............. 5/607, 5/608, 610, 611, 613, 618, 320, 507.1, 83, 5/86, 54, 51, 643, 600–601; 324/300, 306, 324/307, 309, 318, 322, 313; 600/407, 409, 600/421, 410–415; 128/845
See application file for complete search history.

(56) References Cited

U.S. PATENT DOCUMENTS 4,105,923 A 8/1978 Hynes, Jr.
4,534,076 A 8/1985 Barge (Continued)

FOREIGN PATENT DOCUMENTS

JP 1-242056 9/1989

OTHER PUBLICATIONS

Four (4) photographs of an exhibit at the Radiological Society for North America held in Dec. 1996.

(Continued)

*Primary Examiner*—Brian Casler
*Assistant Examiner*—Amanda Lauritzen
(74) *Attorney, Agent, or Firm*—Lerner, David, Littenberg, Krumholz & Mentlik, LLP

(57) ABSTRACT

A positioning system for an MRI system. One aspect includes a support member for moving a patient in a non-horizontal direction within a scanning area of the MRI system, a drive member for driving the support member, and a controller for controlling the drive member to position the patient at a desired location within the scanning area. One aspect includes a guide member attached to a floor beneath the scanning area for guiding a platform member along a first linear axis generally parallel to the floor and perpendicular to a magnetic field axis of a magnet of the MRI system. A controller controls a drive member to position the patient at a desired horizontal location within the scanning area. One aspect includes a frame, a platform member rotatably coupled to the frame. A controller controls a drive member to rotate the platform member and position the patient at a desired angle within the scanning area.

30 Claims, 25 Drawing Sheets

U.S. PATENT DOCUMENTS

| | | | | |
|---|---|---|---|---|
| 4,534,358 | A | 8/1985 | Young | 128/653 |
| 4,567,894 | A | 2/1986 | Bergman | |
| 4,608,991 | A | 9/1986 | Rollwitz | 128/653 |
| 4,613,820 | A | 9/1986 | Edelstein et al. | 324/318 |
| 4,629,989 | A | 12/1986 | Riehl et al. | 324/318 |
| 4,651,099 | A | 3/1987 | Vinegar et al. | 324/320 |
| 4,668,915 | A | 5/1987 | Daubin et al. | 324/309 |
| 4,707,663 | A | 11/1987 | Minkoff et al. | 324/319 |
| 4,727,328 | A | 2/1988 | Carper et al. | |
| 4,766,378 | A * | 8/1988 | Danby et al. | 324/307 |
| 4,777,464 | A | 10/1988 | Takabatashi | 335/306 |
| 4,829,252 | A | 5/1989 | Kaufman | 324/309 |
| 4,875,485 | A * | 10/1989 | Matsutani | 600/415 |
| 4,908,844 | A | 3/1990 | Hasegawa | |
| 4,924,198 | A | 5/1990 | Laskaris | |
| 4,968,937 | A * | 11/1990 | Akgun | 324/318 |
| 4,985,678 | A | 1/1991 | Gangarosa et al. | 324/318 |
| 5,008,624 | A * | 4/1991 | Yoshida | 324/318 |
| 5,061,897 | A | 10/1991 | Danby et al. | 324/318 |
| 5,065,761 | A | 11/1991 | Pell | 128/660.03 |
| 5,124,651 | A | 6/1992 | Danby et al. | 324/318 |
| 5,150,710 | A * | 9/1992 | Hall et al. | 600/422 |
| 5,153,546 | A | 10/1992 | Laskaris | 335/216 |
| 5,155,758 | A | 10/1992 | Vogl | |
| 5,162,768 | A | 11/1992 | McDougall et al. | 335/296 |
| 5,194,810 | A | 3/1993 | Breneman et al. | 324/319 |
| 5,197,474 | A * | 3/1993 | Englund et al. | 600/415 |
| 5,207,224 | A | 5/1993 | Dickinson et al. | 128/653.5 |
| 5,210,893 | A * | 5/1993 | Uosaki et al. | 5/601 |
| 5,229,723 | A | 7/1993 | Sakurai et al. | 324/319 |
| 5,250,901 | A | 10/1993 | Kaufman et al. | 324/318 |
| 5,259,011 | A | 11/1993 | Petro | |
| 5,291,890 | A | 3/1994 | Cline et al. | 128/653.2 |
| 5,305,365 | A | 4/1994 | Coe | |
| 5,305,749 | A | 4/1994 | Li et al. | 128/653.2 |
| 5,315,276 | A | 5/1994 | Huson et al. | 335/216 |
| 5,349,956 | A | 9/1994 | Bonutti | |
| 5,382,904 | A | 1/1995 | Pissanetzky | 324/319 |
| 5,386,447 | A | 1/1995 | Siczek | |
| 5,412,363 | A | 5/1995 | Breneman et al. | 335/216 |
| 5,436,607 | A | 7/1995 | Chari et al. | 335/216 |
| 5,475,885 | A | 12/1995 | Ishikawa | |
| 5,490,513 | A | 2/1996 | Damadian et al. | 128/653.2 |
| 5,519,372 | A | 5/1996 | Palkovich et al. | |
| 5,592,090 | A | 1/1997 | Pissanetzky | 324/319 |
| 5,606,970 | A | 3/1997 | Damadian | 128/653.2 |
| 5,623,241 | A | 4/1997 | Minkoff | |
| 5,624,159 | A | 4/1997 | Celoni et al. | |
| 5,640,958 | A | 6/1997 | Bonutti | |
| 5,680,861 | A * | 10/1997 | Rohling | 600/407 |
| 5,735,278 | A * | 4/1998 | Hoult et al. | 600/422 |
| 5,743,264 | A | 4/1998 | Bonutti | |
| 5,779,637 | A | 7/1998 | Palkovich et al. | |
| 5,825,843 | A | 10/1998 | Kobayashi et al. | |
| 5,926,876 | A * | 7/1999 | Haigh et al. | 5/617 |
| 5,983,424 | A * | 11/1999 | Naslund | 5/601 |
| 6,003,174 | A * | 12/1999 | Kantrowitz et al. | 5/601 |
| 6,014,070 | A | 1/2000 | Danby et al. | |
| 6,023,165 | A | 2/2000 | Damadian et al. | |
| 6,094,760 | A * | 8/2000 | Nonaka et al. | 5/601 |
| 6,198,957 | B1 * | 3/2001 | Green | 600/411 |
| 6,246,239 | B1 | 6/2001 | Krogmann et al. | |
| 6,249,695 | B1 * | 6/2001 | Damadian | 600/427 |
| 6,335,623 | B1 | 1/2002 | Damadian et al. | |
| 6,356,081 | B1 * | 3/2002 | Misic | 324/318 |
| 6,385,481 | B2 * | 5/2002 | Nose et al. | 600/415 |
| 6,411,088 | B1 | 6/2002 | Kuth et al. | |
| 6,414,490 | B1 | 7/2002 | Damadian et al. | |
| 6,456,075 | B1 * | 9/2002 | Damadian et al. | 324/318 |
| 6,496,007 | B1 | 12/2002 | Damadian et al. | |
| 6,504,371 | B1 * | 1/2003 | Damadian et al. | 324/318 |
| 6,534,982 | B1 * | 3/2003 | Jakab | 324/318 |
| 6,675,037 | B1 * | 1/2004 | Tsekos | 600/417 |
| 6,677,753 | B1 | 1/2004 | Danby et al. | |
| 6,806,712 | B2 | 10/2004 | Akgun | |
| 6,828,792 | B1 * | 12/2004 | Danby et al. | 324/318 |
| 6,934,574 | B1 * | 8/2005 | Damadian et al. | 600/415 |
| 6,986,179 | B2 * | 1/2006 | Varadharajulu et al. | 5/611 |
| 7,123,008 | B1 * | 10/2006 | Damadian et al. | 324/309 |
| 7,239,906 | B1 * | 7/2007 | Green et al. | 600/407 |
| 2003/0204136 | A1 * | 10/2003 | Green et al. | 600/415 |
| 2004/0030241 | A1 * | 2/2004 | Green et al. | 600/422 |
| 2004/0138553 | A1 * | 7/2004 | Damadian | 600/410 |
| 2005/0187459 | A1 * | 8/2005 | Trequattrini et al. | 600/415 |
| 2005/0222505 | A1 * | 10/2005 | Damadian et al. | 600/415 |
| 2005/0285595 | A1 | 12/2005 | Green et al. | |
| 2006/0173278 | A1 * | 8/2006 | Wahl et al. | 600/410 |
| 2008/0161676 | A1 * | 7/2008 | Satragno et al. | 600/415 |

OTHER PUBLICATIONS

Green et al., U.S. Appl. No. 10/301,197, filed Nov. 21, 2002.

* cited by examiner

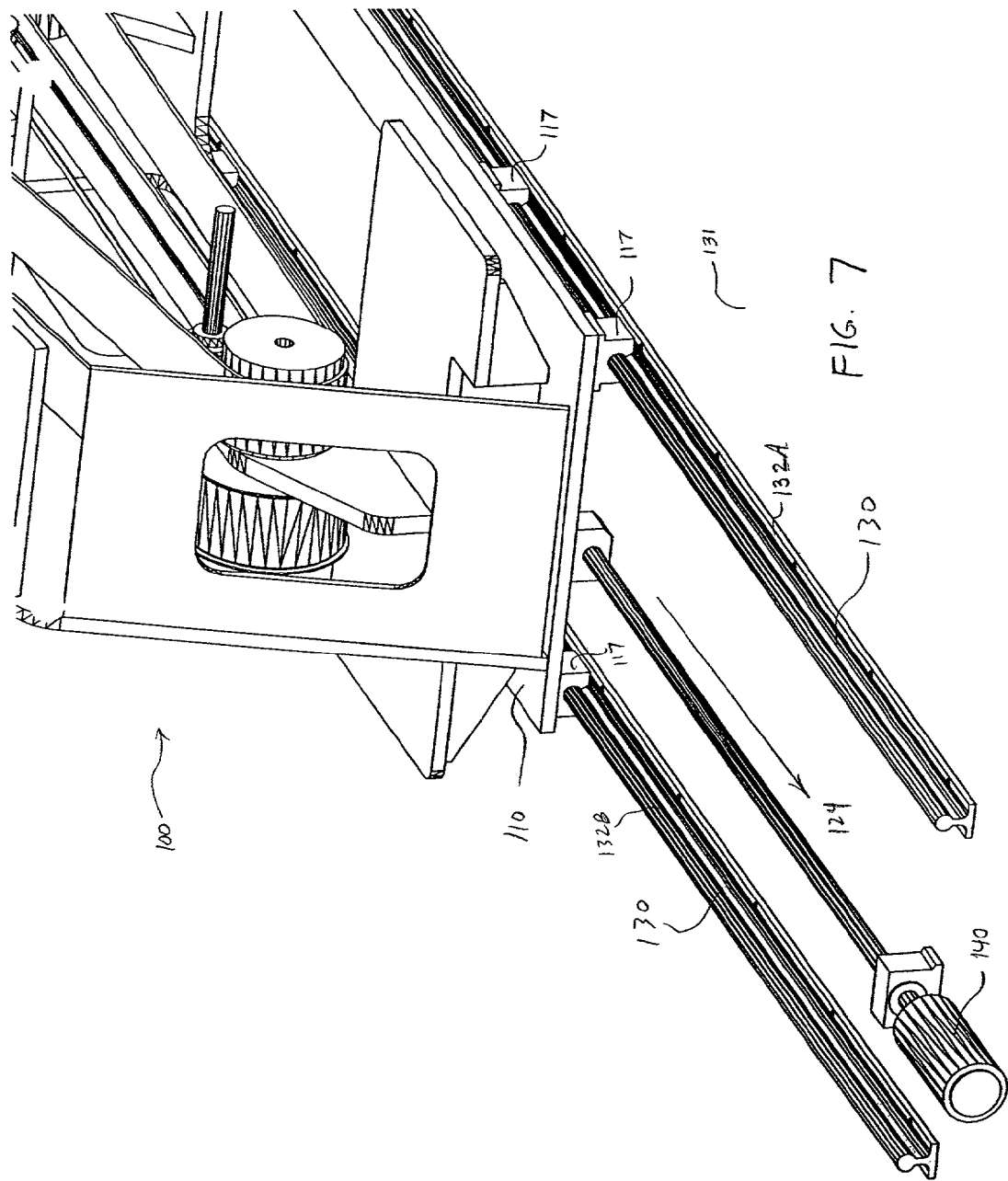

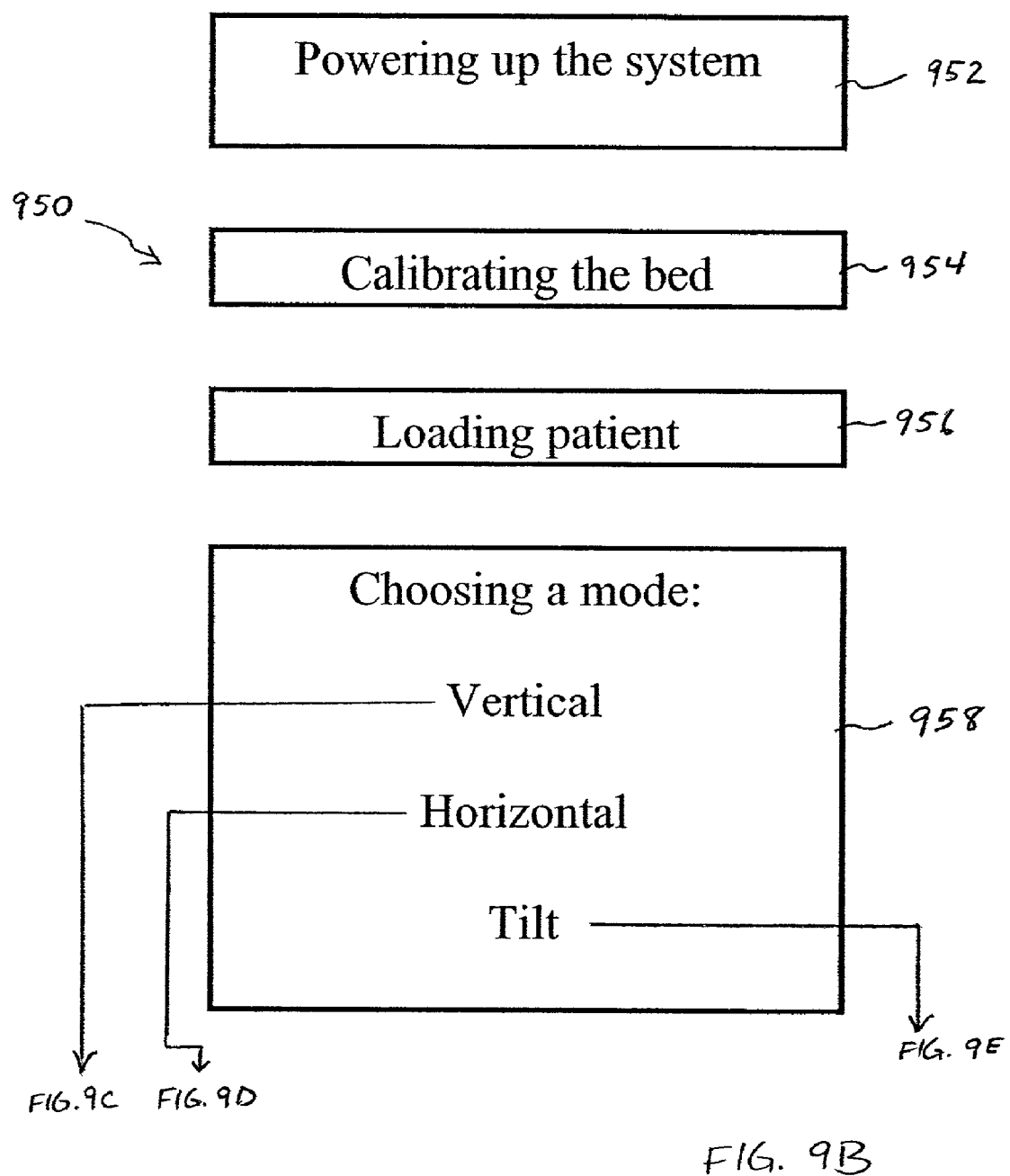

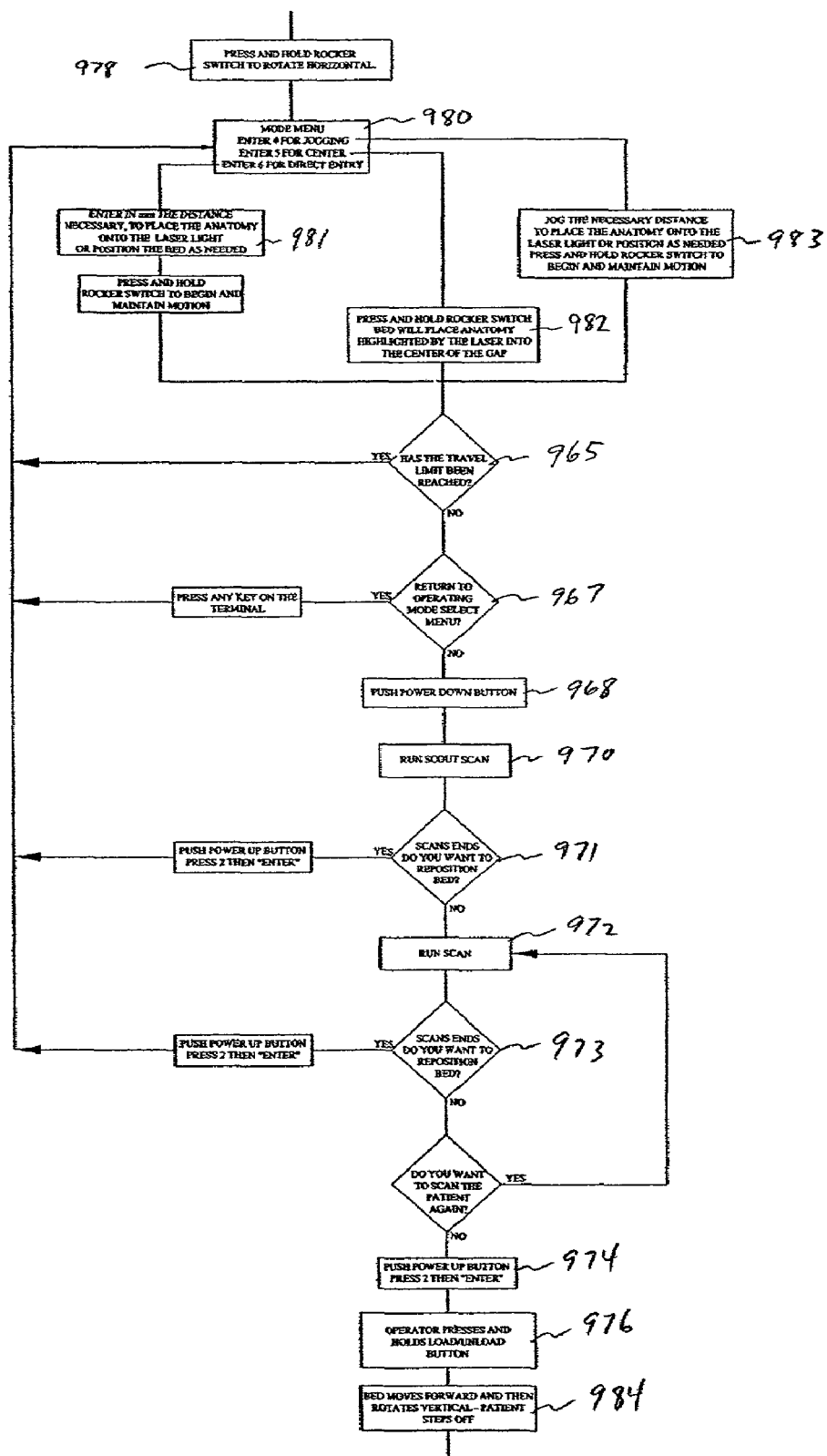

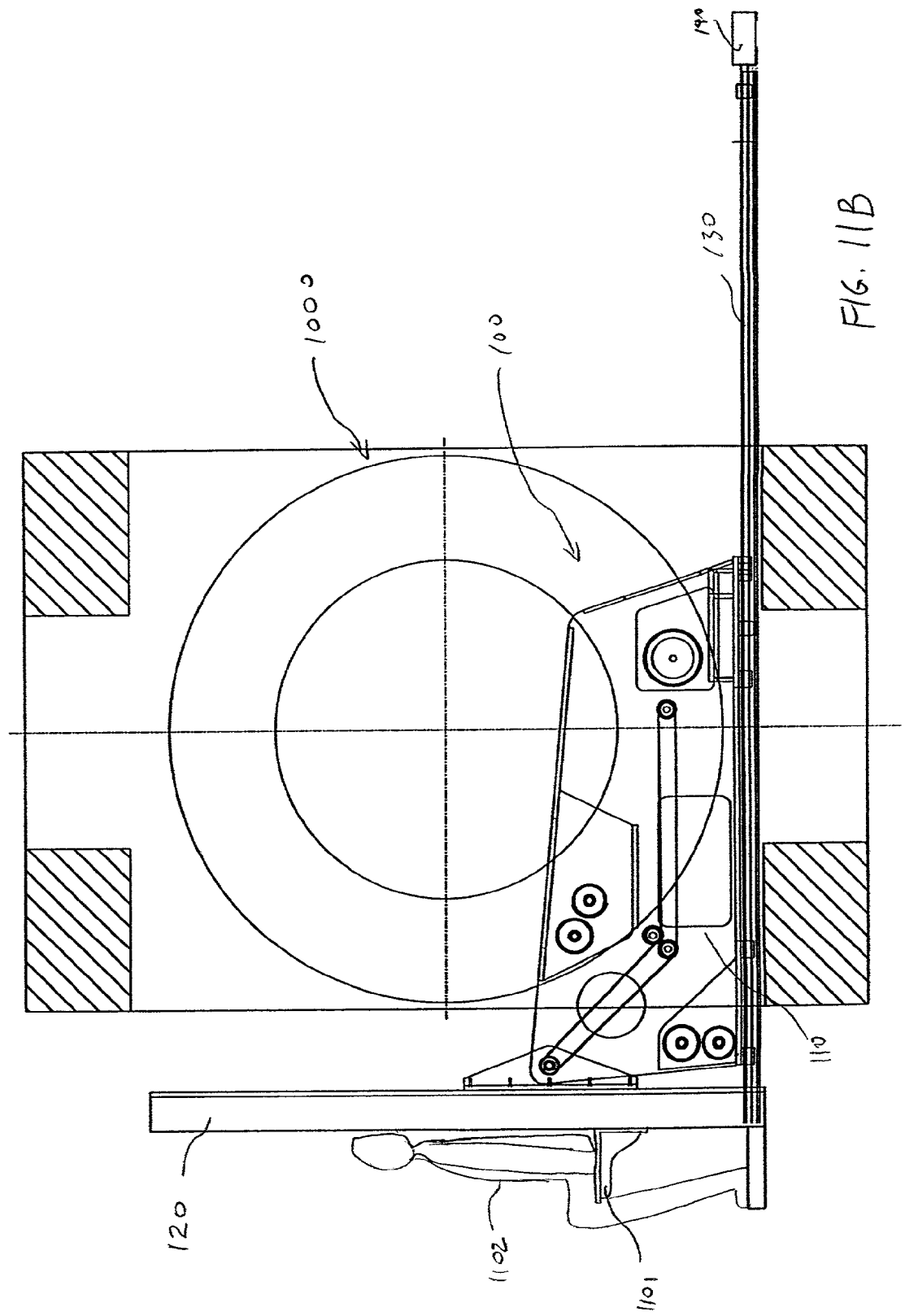

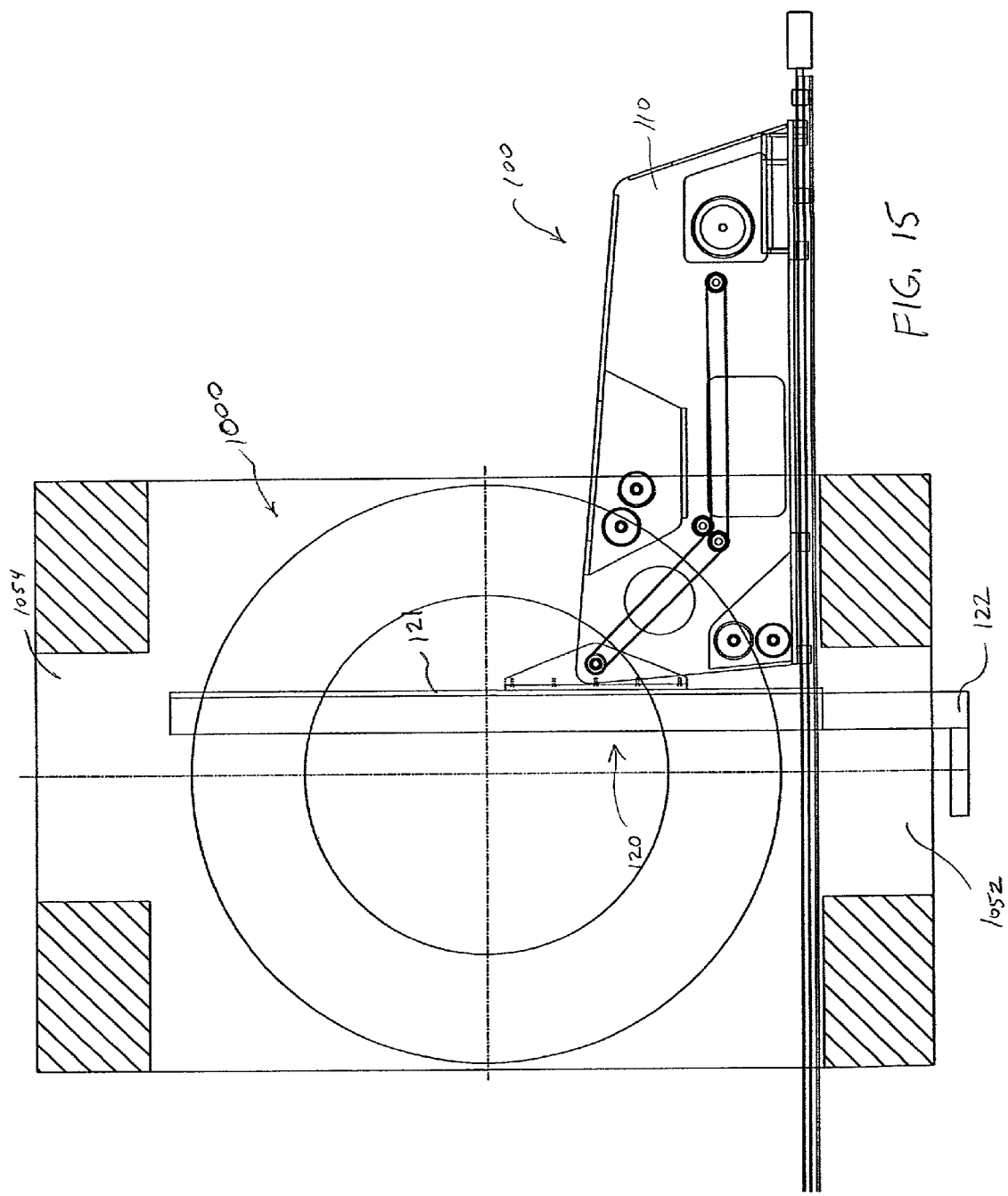

POSITIONING SYSTEM FOR AN MRI

CROSS-REFERENCES TO RELATED APPLICATIONS

This application claims the benefit under 35 U.S.C. 119(e) of U.S. Provisional Application Ser. No. 60/222,098 filed Jul. 28, 2000, and U.S. Provisional Application Ser. No. 60/252,837 filed Nov. 22, 2000, both of which are incorporated herein by reference in their entireties. This application also incorporates by reference and is a continuation-in-part of U.S. patent application Ser. No. 09/718,946, filed Nov. 22, 2000 now U.S. Pat. No. 6,677,753. This application also incorporates by reference U.S. patent application Ser. No. 08/978,084, filed Nov. 25, 1997.

FIELD OF THE INVENTION

This invention relates generally to the field of MRI systems, and more specifically to a patient handling and positioning system for an MRI.

BACKGROUND

Patients receiving various medical diagnoses or treatments often need to be positioned correctly to properly receive the diagnosis or treatment. For instance, magnetic resonance imaging (MRI) systems require that the portion of the anatomy to be scanned be positioned within a relatively small imaging volume. One problem with some present patient positioning systems is that it is difficult to consistently and accurately locate the patient within the imaging volume to obtain a high quality image.

Moreover, MRI scanners generally require the patient to be oriented with the long axis of the body in a horizontal position. However, other positions of the body, such as vertical, an in-between angle, the Trendelenburg or reverse Trendelenburg positions, or sitting are also desirable.

Another problem is that present systems are limited in the number of positions a patient can be located in and there is no simple method of changing positions quickly for a variety of patients.

SUMMARY

Accordingly, methods and structures for patient handling and positioning have been devised which provide, among other advantages, faster, more accurate, and/or more variable positioning of patients in MRI systems or other systems requiring accurate patient positioning.

One aspect of the present invention includes a support member for moving a patient in a non-horizontal direction within a scanning area of the MRI system, a drive member for driving the support member, and a controller for controlling the drive member to position the patient at a desired location within the scanning area. One aspect includes a guide member attached to a floor beneath the scanning area for guiding a platform member along a first linear axis generally parallel to the floor and perpendicular to a magnetic field axis of a magnet of the MRI system. A controller controls a drive member to position the patient at a desired horizontal location within the scanning area. One aspect includes a frame and a platform member rotatably coupled to the frame. A controller controls a drive member to rotate the platform member and position the patient at a desired angle within the scanning area.

One aspect provides a positioning system which includes a frame and a platform member rotatably coupled to the frame. The system also includes means for movement and indexing on a first linear axis, means for movement on a second linear axis, and means for rotating. Among other advantages, the exemplary positioning system provides for fast, accurate movement between different positions, such as between vertical, horizontal, Trendelenburg, or in between.

BRIEF DESCRIPTION OF THE DRAWINGS

FIG. 7 shows a rear isometric cut-away view of portions of the positioning system of FIG. 1.

FIGS. 9B-9E show a flowchart representation of a method for positioning the positioning system according to one embodiment of the present system.

FIG. 11B shows a side view of the positioning system of FIG. 1 having a removable seat attached.

FIG. 15 shows another side view of the positioning system of FIG. 1 located within an exemplary MRI magnet.

DETAILED DESCRIPTION

The following detailed description, which references and incorporates the figures, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

Figure 1:
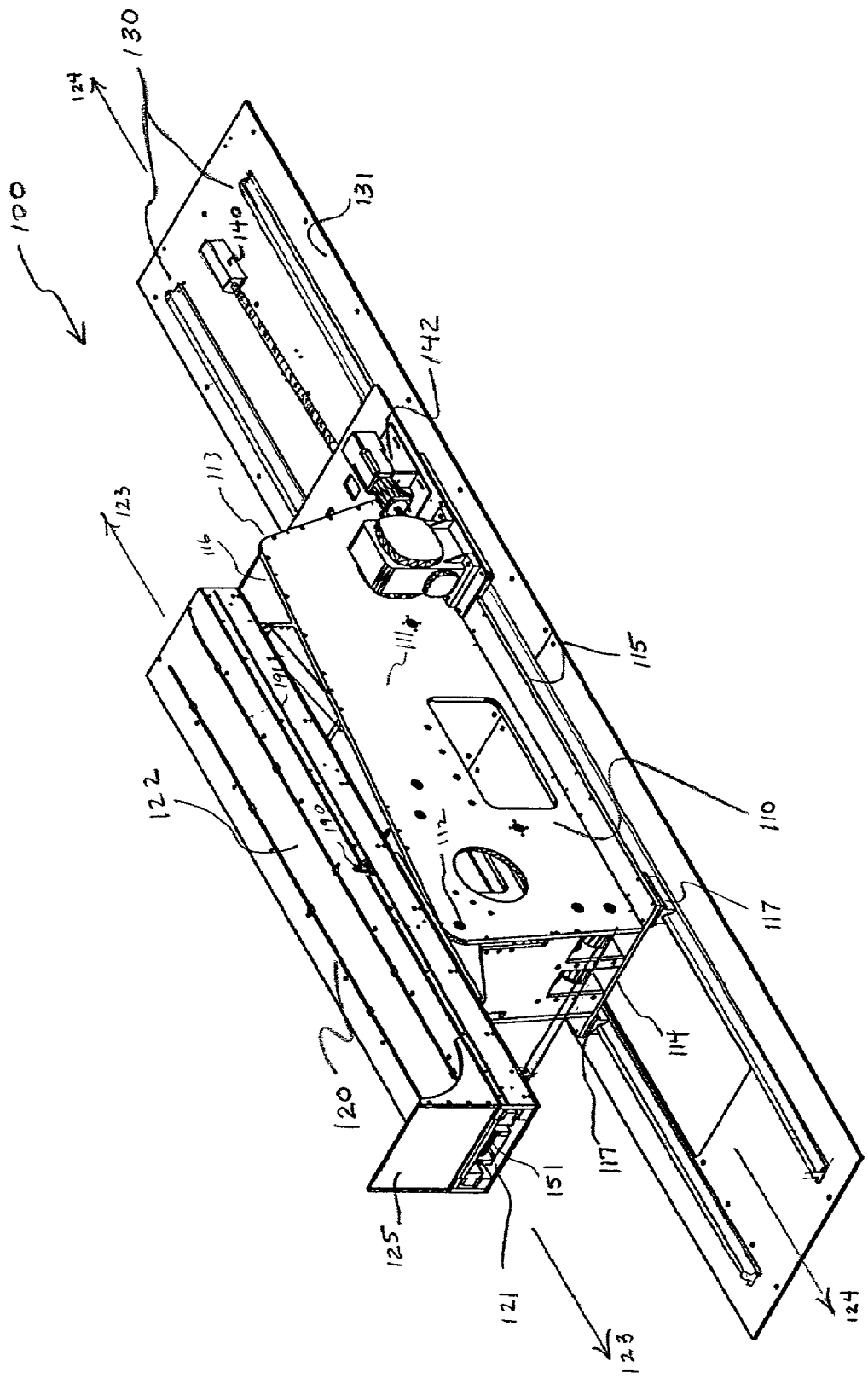
FIG. 1 shows a front isometric view of a positioning system according to one embodiment of the present invention.
Figure 2A:
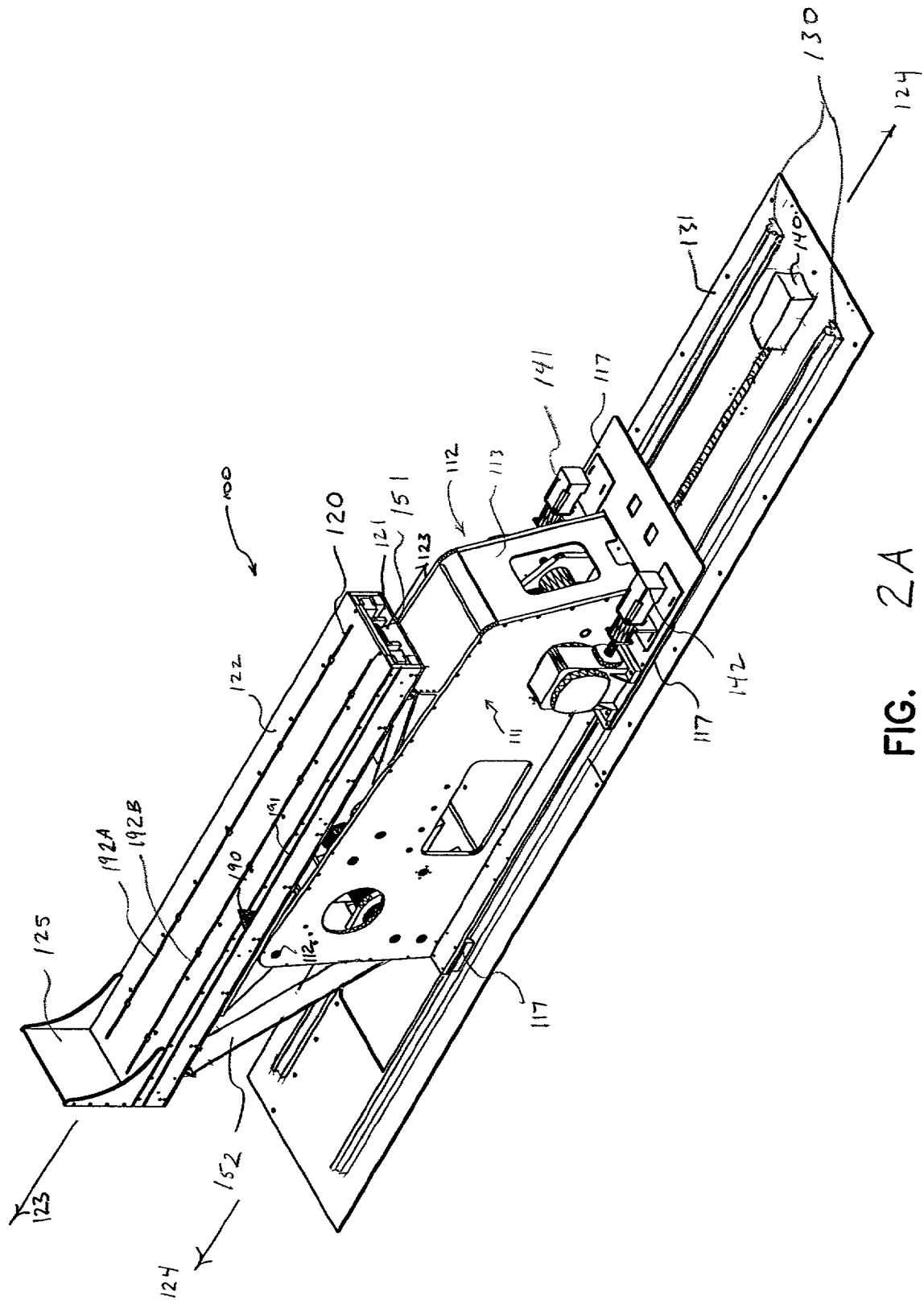
FIG. 2A shows a rear isometric view of the positioning system of FIG. 1.

FIGS. 1 and 2A show a patient handling system or MRI positioning system 100 according to one embodiment. Positioning system 100 is a multi-axis positioning system, which can be used to articulate a patient's anatomy in various orientations. In various embodiments, the present system can be used for positioning humans, animals, inanimate objects and so on. Accordingly, the term patient generally includes any object being positioned by the system.

MRI positioning system 100 includes a frame 110—also referred to herein as the carriage frame—and a platform member 120, which is movable along a first linear axis 123, a second linear axis 124 and a rotational axis 112. In the exemplary embodiment, the movement of carriage frame 110 and platform member 120 along and around these various axes is provided by a guide member 130, a first drive member 140, a second drive member 141, a third drive member 142, a first belt 151, and a second belt 152. Drive members 140-142 can include electric motors, servo-motors, stepper motors, and other equivalent drivers. Some embodiments of the present invention omit one or more of these features.

In one embodiment, carriage frame 110 has a generally rectangular box-shape. Frame 110 includes a first side 111, a second side 112, a back side 113, a front side 114, a bottom side 115 and a top side 116. Frame 110 is manufactured from nonmagnetic material such as PVC, G10, wood, or other material. In the exemplary embodiment, frame 110 includes a plurality of members 117 for guiding the frame along guide member 130.

Platform member 120 is rotatably coupled to carriage frame 110 about a horizontal axis 112. Platform member 120 is rotatable from an approximately horizontal orientation relative to floor 131 to an approximately vertical orientation. In some embodiments, platform member rotates around axis 112 with a range of rotation which overshoots or undershoots the horizontal and/or vertical orientations by about 5 degrees or greater. Among other advantages, this allows a patient to be placed in the Trendelenburg or reverse Trendelenburg positions. In one embodiment, axis point 112 is approximately 30 inches above the floor. Other embodiments vary the axis height depending on the use of system 100.

In one embodiment, platform member 120 is rotated around axis 112 by driving member 142 coupled with belt 152. In other embodiments, platform 120 is rotated around axis 112 by manual rotation, air or hydraulic actuation, counter weights, springs, direct drive to the rotational shaft at axis 112 via a drive belt, and/or a gearing system which can include a sector gear and a rack and pinion.

Platform 120 includes a platform frame 121, which is coupled to carriage frame 110, and a patient holding or support member such as slab 122, which is a flat, unitary member designed for supporting and holding a patient. In one embodiment, slab 122 includes a cushioned surface. For instance, a pad or mat can be integral with or mounted on top of the slab. Another embodiment provides a cushioned surface made from a form-fitting, pressure-relieving material, such as a Tempur-Pedic brand mattress or pad manufactured by Tempur-Pedic Inc.

In the exemplary embodiment, coupled to slab 122 is a second platform or foot-stand 125, which is generally perpendicular to platform member 120. Foot-stand 125 is for a patient to stand on while being positioned for scanning and while scanning. Platform frame 121 is coupled to frame 110 while slab 122 slides along first linear axis 123, which is linear relative to a longitudinal axis of platform frame 121. In the exemplary embodiment, slab 122 is driven along the linear axis of platform frame 121 by driving member 141 coupled with belt 151. In some embodiments, the linear motion of slab 122 is provided by a ball screw located in the platform slab, air or hydraulic actuation, counter weights, stored energy springs, and/or a rack and pinion coupling between a rotational shaft and the slab.

Coupled to platform member 120 is a positioner 190 which travels within a slot 191 on the side of the platform member. Details of positioner 190 will be discussed below. Slab 122 also includes one or more connection mechanisms 192A and 192B. The connection mechanisms are for attaching external hardware such as RF coils, patient restraining means, or other devices to the platform. In some embodiments, slab 122 also includes a plurality of holes, notches, or other locating features for attaching other peripherals, such as removable seats or restraining devices to the platform. In one embodiment, connection mechanisms 192A and 192B can include a series of discrete connection points along the slab allowing hardware to be mounted at substantially any location along the support member. In other embodiments, connection mechanism 192A and 192B are elongated slots which provide a continuously variable mounting area along the support member.

In the exemplary embodiment, driving member 142 is located on first side 111 of frame 110 and driving member 141 is located on the second side 112 of frame 110. In some embodiments, both are located on the same side or on the back side 113 of frame 110, as will be described below. In the exemplary embodiment, drive members 141 and 142 are electric motors which drive belts 151 and 152, respectively. Belts 151 and 152 are a very low stretch, tight tolerance material. In one embodiment, belts 151 and 152 have a toothed surface. Drive members 141 and 142 are located relatively close to the floor and away from the portion of the system 100 that will be in the middle of the magnetic field of the MRI magnet when a patient is being scanned. Advantageously, the location of the driving members and the shape of the belts help keep the driving members from interfering with any magnetic or RF signals.

Figure 2B:
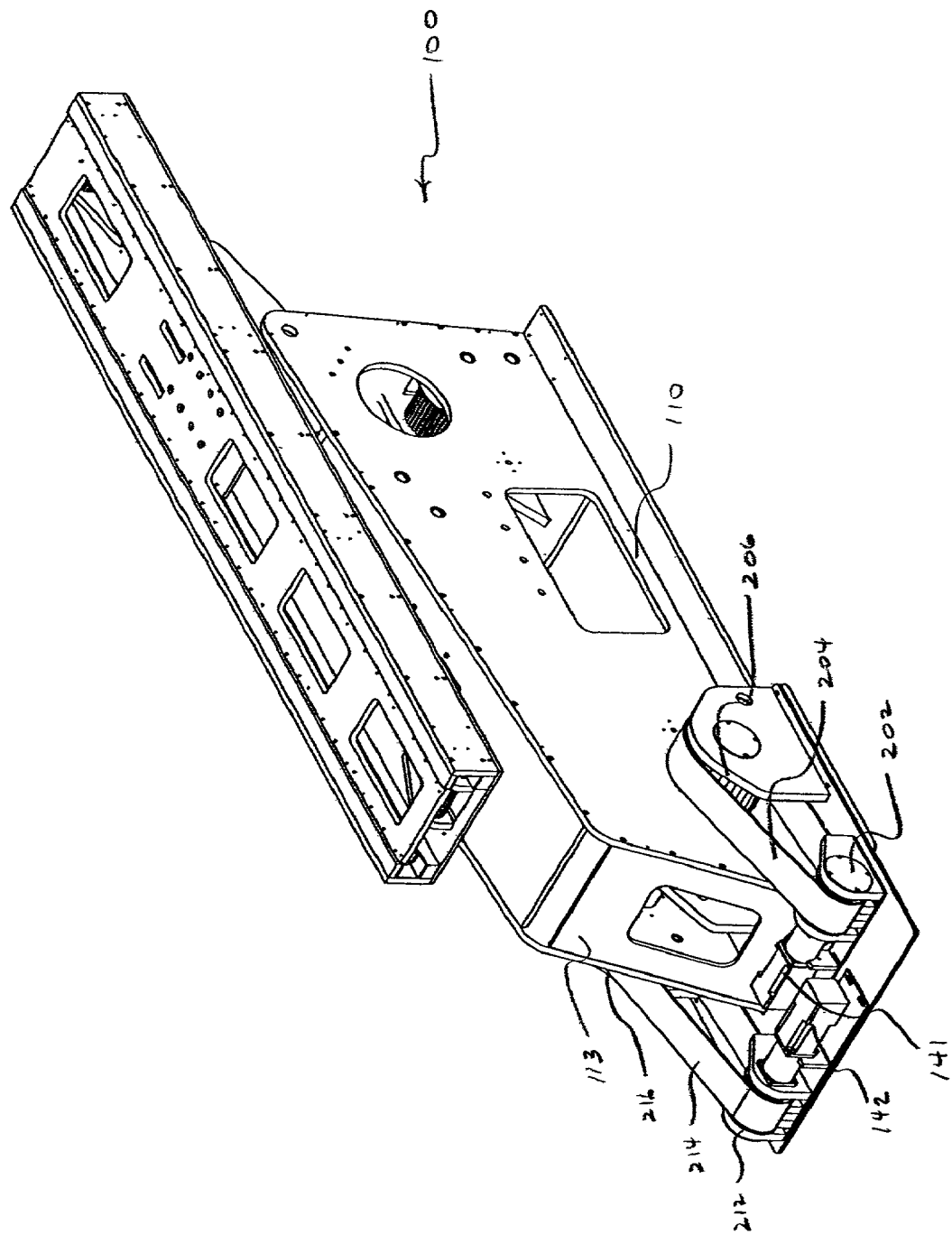
FIG. 2B shows a rear isometric view of a positioning system according to one embodiment of the present invention.

FIG. 2B shows a rear isometric view of MRI positioning system 100 according to another embodiment of the present invention. In this embodiment, drive members 141 and 142 are located on the back side 113 of frame 110. Drive member 141 drives a gear or pulley 202 which is connected by a drive belt 204 to a gear or pulley 206. Drive member 142 drives a gear or pulley 212 which is connected by a drive belt 214 to a gear or pulley 216. Gears 206 and 216 are connected to internal gears and belts within frame 110, as will be discussed below. The location of drive members 141 and 142 in the present embodiment provide that the drive members are even further removed from the magnetic field of an MRI system when frame 110 is directed within the magnetic field of the system.

Figure 2C:
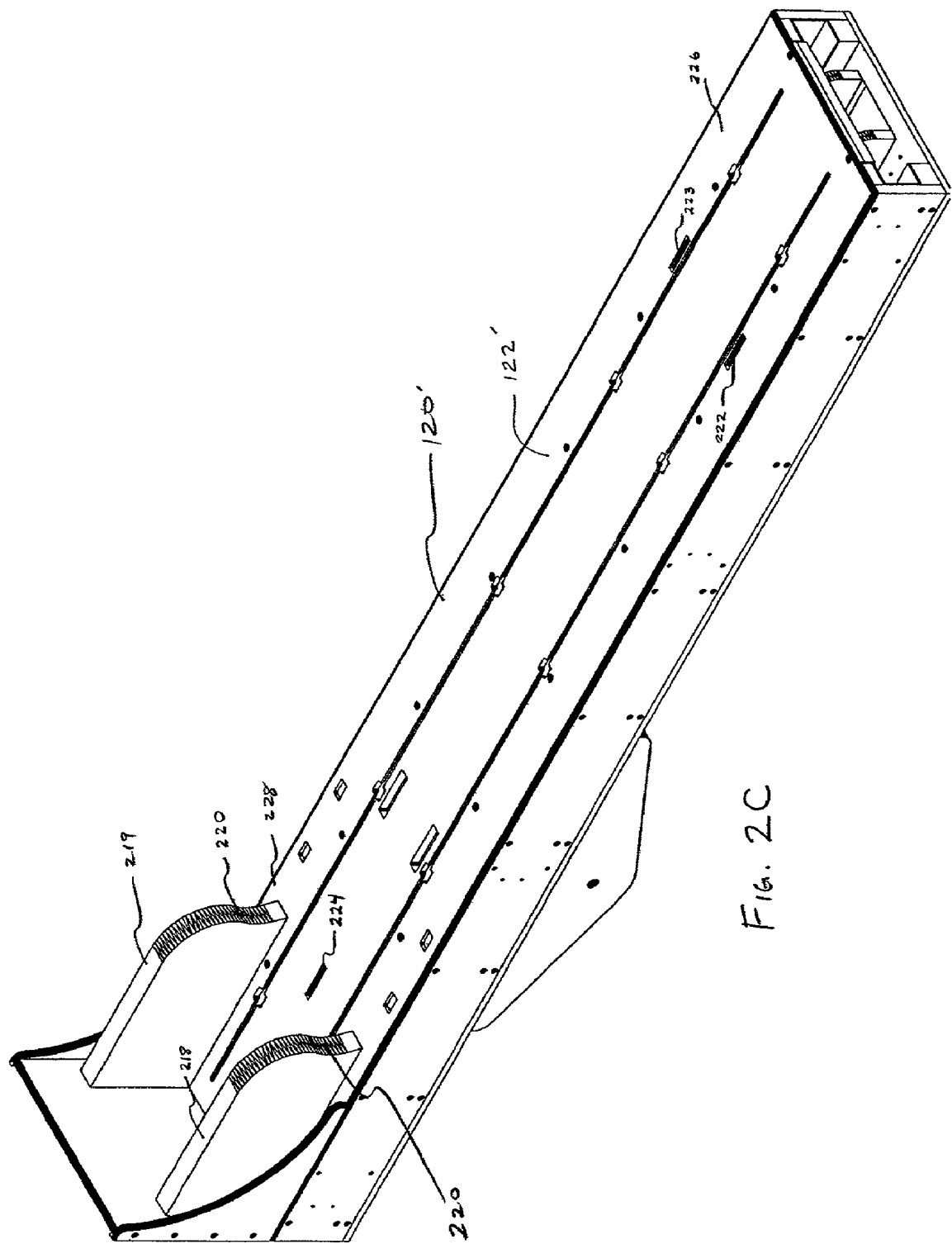
FIG. 2C shows an isometric view of a platform according to one embodiment.

FIG. 2C shows an isometric view of a platform member 120' according to one embodiment. Platform member 120' includes optional supports 218 and 219. In one embodiment, supports 218 and 219 are attached to platform 120' and are padded or cushioned to provide cushioning and support for a patient's shoulders when the patient is oriented in the Trendelenburg position. Supports 218 and 219 are removable and can be dimensioned in various sizes for different sizes of patients. For instance, in some embodiments, supports 218 and 219 are sized for the shoulders of an adult male. Other supports 218 and 219 are dimensioned for the shoulders of a small child. In one embodiment, a curved edge 220 is provided on one or more of supports 218 and 219 to help situate and position the patient properly and comfortably upon platform 120'. In one example use of supports 218 and 219, a patient is loaded on the platform in a horizontal position, the patient's shoulders are abutted against supports 218 and 219, and the platform is tilted into the Trendelenburg position.

In one embodiment, platform member 120' also includes one or more connection ports 222. In one embodiment, three connection ports 222, 223, and 224 are provided. Other embodiments include fewer or more ports than shown for platform 120'. In one embodiment, connection ports 222-224 are directly attached to slab 122' of platform 120' to provide an uncomplicated connection for RF coils and/or other components to be described below. In this example, two connection ports are provided on a first end 226 of platform 120' and one connection port is provided on a second end 228.

Figure 2D:
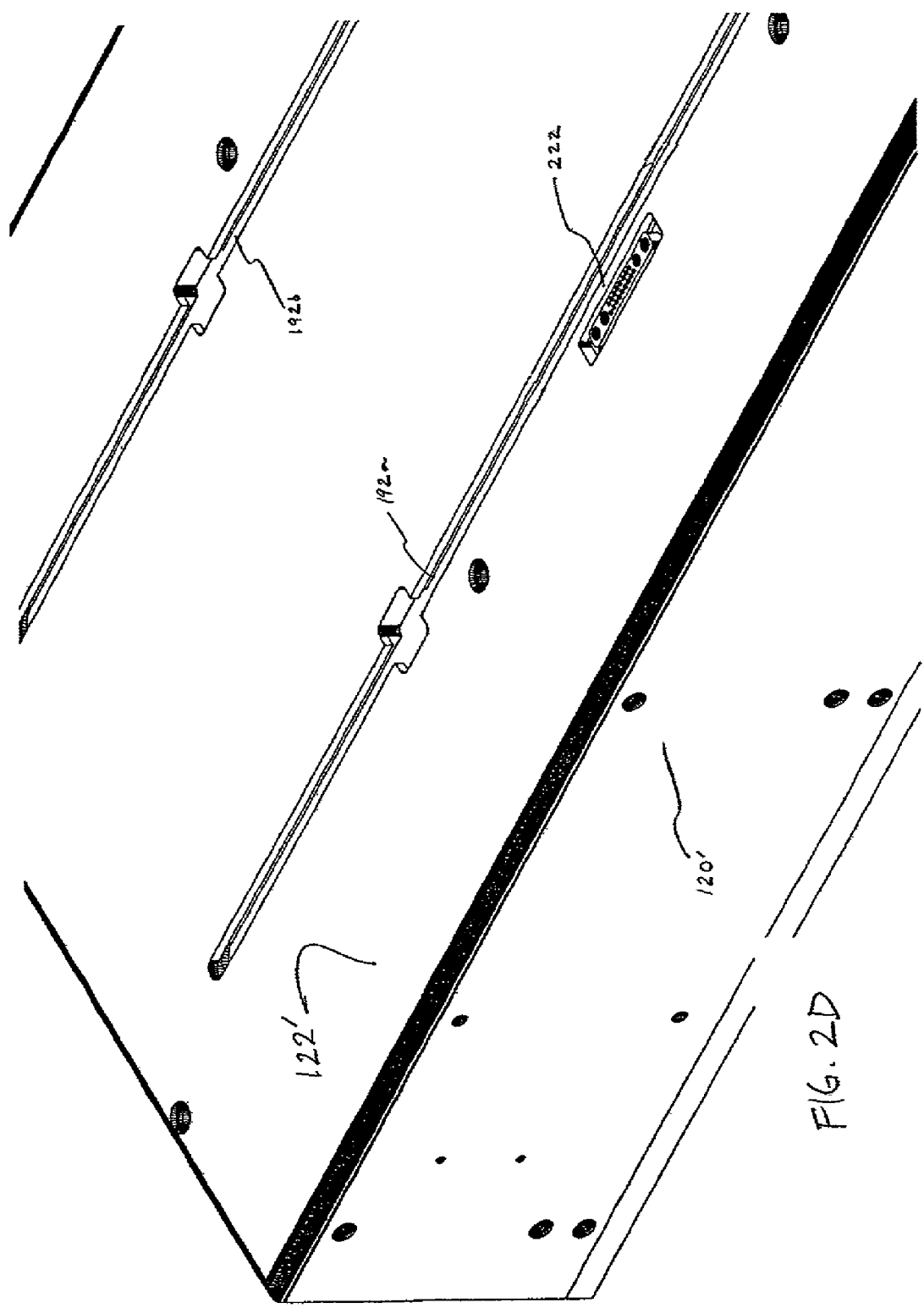
FIG. 2D shows details of a connection port of FIG. 2C.

FIG. 2D shows a close-up of details of connection port 222 on slab 122' of platform 120'.

Figure 2E:
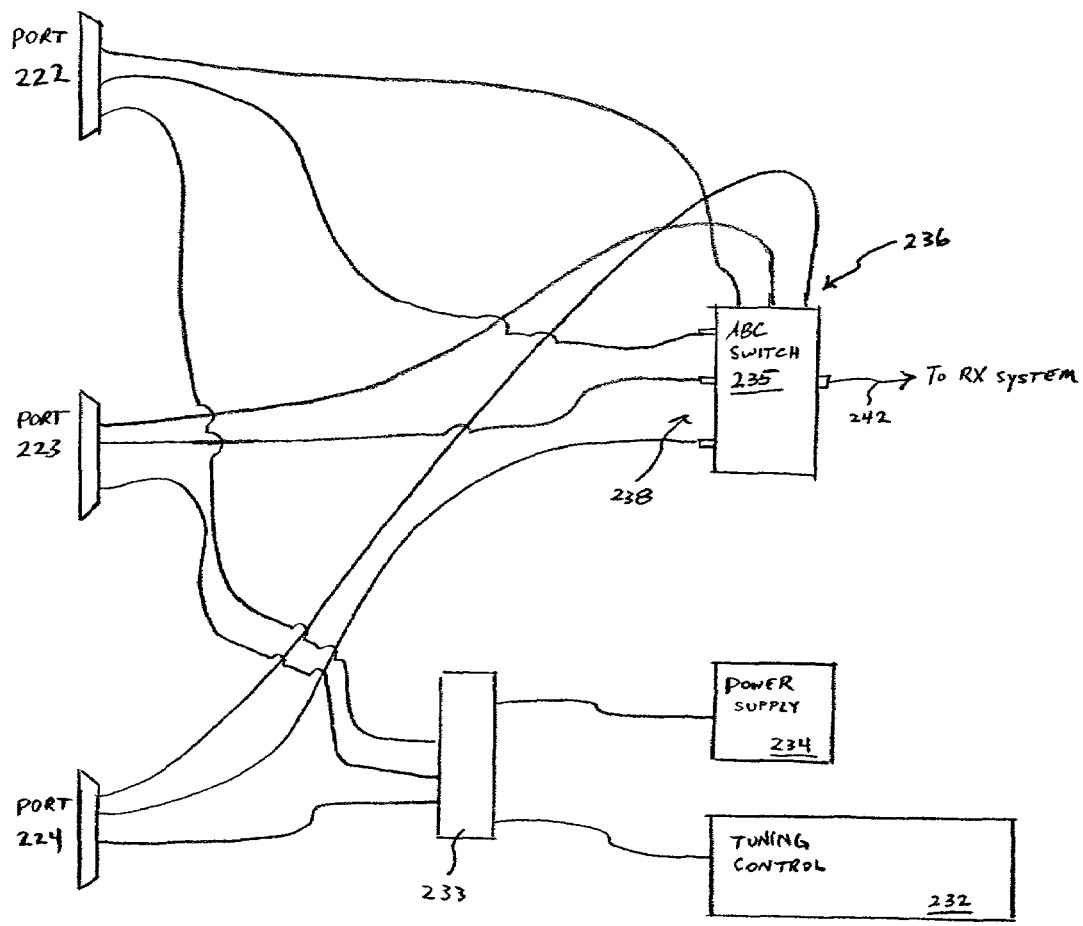
FIG. 2E shows a schematic drawing of connections between the connection ports of FIG. 2C and a receiver system, according to one embodiment.

FIG. 2E shows a schematic drawing of an example connection between the connection ports 222-224 of FIG. 2C and a receiver system, RX. In one embodiment, each of ports 222-224 is an RF connection port connected to a tuning control 232 and a power supply 234 via a connector 233. Each of ports 222-224 is also connected to an ABC switch 235. In one embodiment, switch 235 includes an input control section 236, connection ports 238, and a connection 242 to the receiver system RX. By directly mounting connection ports 222-224 on platform 120' and providing connections to the receiver system, the present embodiment simplifies the connection of, and signal processing for, any RF coils or other components coupled to the system.

Figure 3:
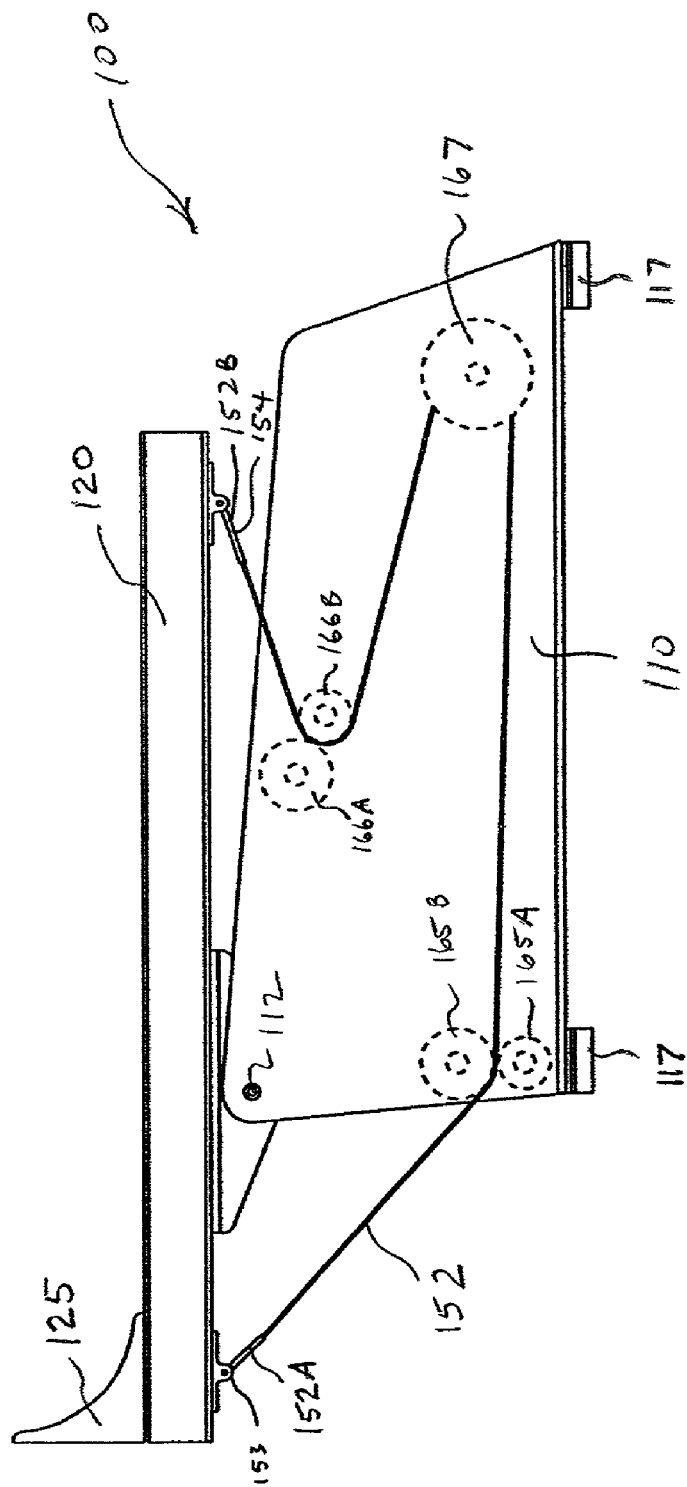
FIG. 3 shows a side view of the positioning system of FIG. 1.

FIG. 3 shows a side view of MRI positioning system 100 with details of an exemplary connection of belt 152. Belt 152 has a first end 152A connected to a first end of platform frame 120 at connector 153 and a second end 152B connected to the other end of the platform frame at a connector 154. Belt 152 runs between lower pulleys 165A and 165B and upper pulleys 166A and 166B. When drive member 142 (FIG. 2A) is activated, it drives a drive gear 167 which drives belt 152 which pulls on either end of the platform and thereby rotates the platform around axis 112. In the exemplary embodiment, the pulleys and gears are manufactured from aluminum. In some embodiments, they are plastic or other non-magnetic material.

Figure 4:
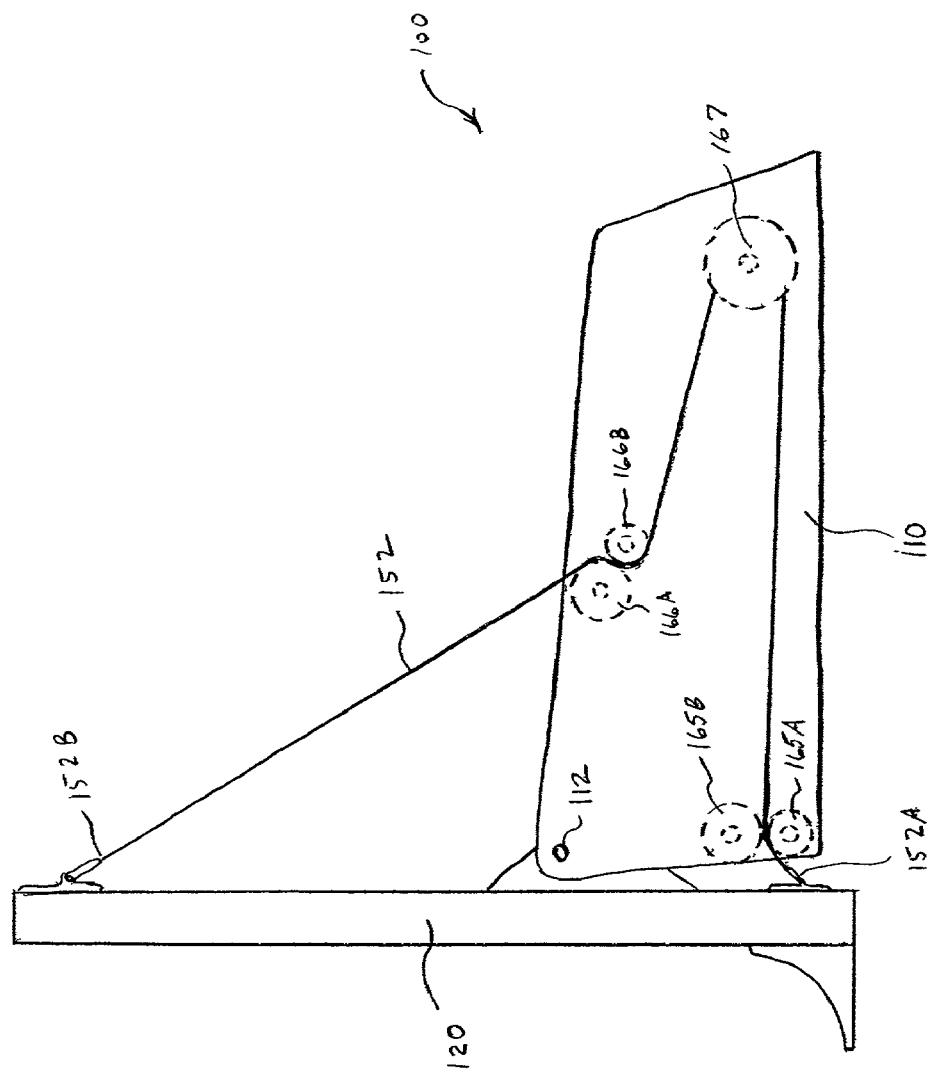
FIG. 4 shows another side view of the positioning system of FIG. 1.

FIG. 4 shows another side view of positioning system 100 with platform 120 rotated to a vertical position. In one embodiment, a sensor and controller are coupled to drive member 142 (FIG. 2A) for sensing and controlling the position of the platform member as it rotates around the horizontal axis. For instance, a counter such as an encoder is coupled to the driving member to count the number of rotations of the motor, which corresponds to a set number of degrees of rotation of the platform.

Figure 5:
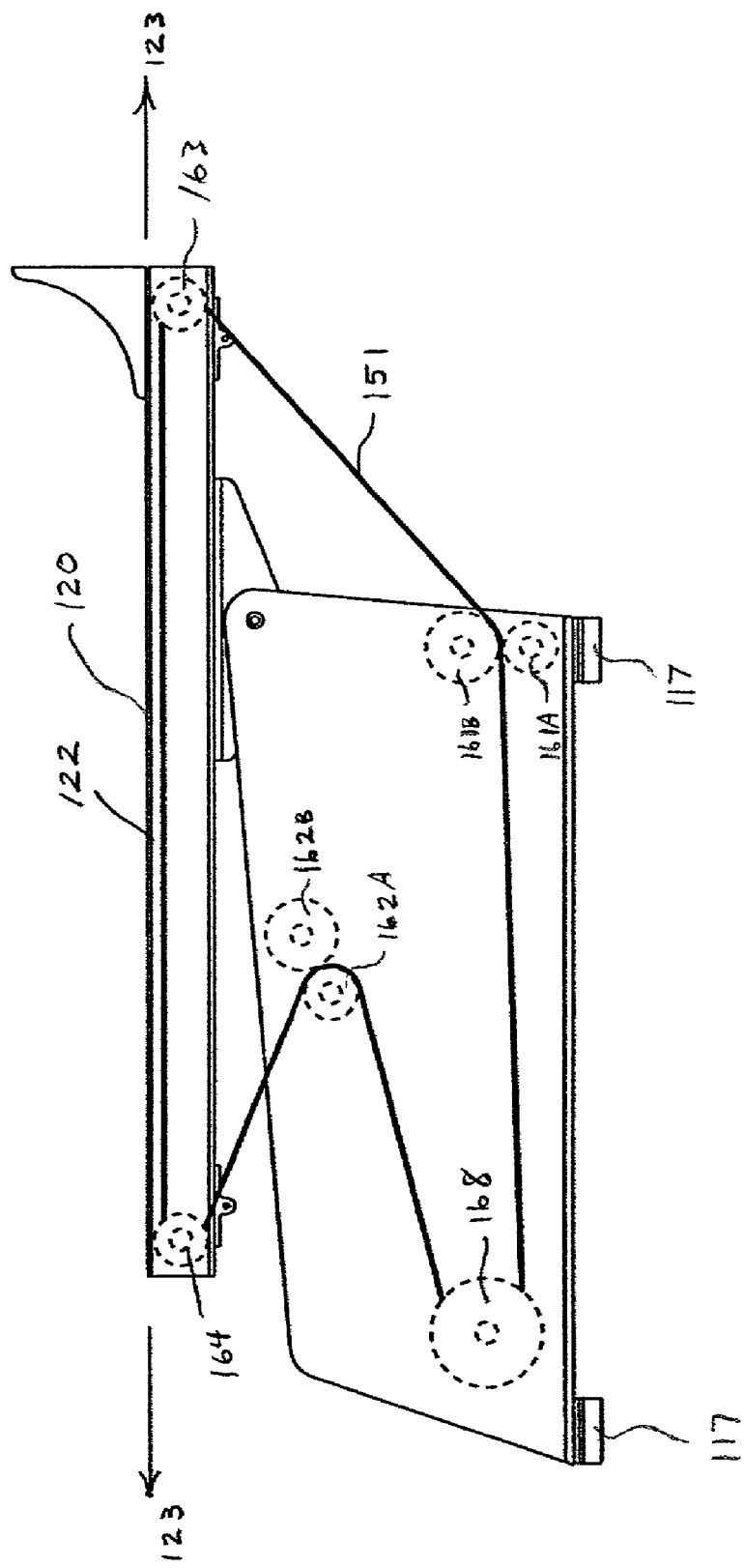
FIG. 5 shows another side view of the positioning system of FIG. 1.

FIG. 5 shows a side view of positioning system 100 showing exemplary details of drive belt 151. Driving member 141 (FIG. 2A) drives belt 151 in a loop via a drive gear 168. The belt goes around lower idler pulleys 161A and 161B then around a pulley 163 located near one end of platform member 120 and on through a pulley 164 at the other end of platform member 120 then through upper idler pulleys 162A and 162B and back to main driving gear 168. Slab 122 is coupled to drive belt 151 so as the drive belt is driven, slab 122 linearly moves along platform 120 along first linear axis 123.

In one embodiment, driving member 141 (FIG. 2A) is coupled to a sensor and a controller for sensing or detecting the position of slab 122. For instance, in one embodiment, a sensor such as an encoder counts the rotations of the motor of the driving member and stores the information so that the exact location and position of slab 122 is readily ascertainable and controllable. In one embodiment, the controller calculates the position and controls it.

Figure 6:
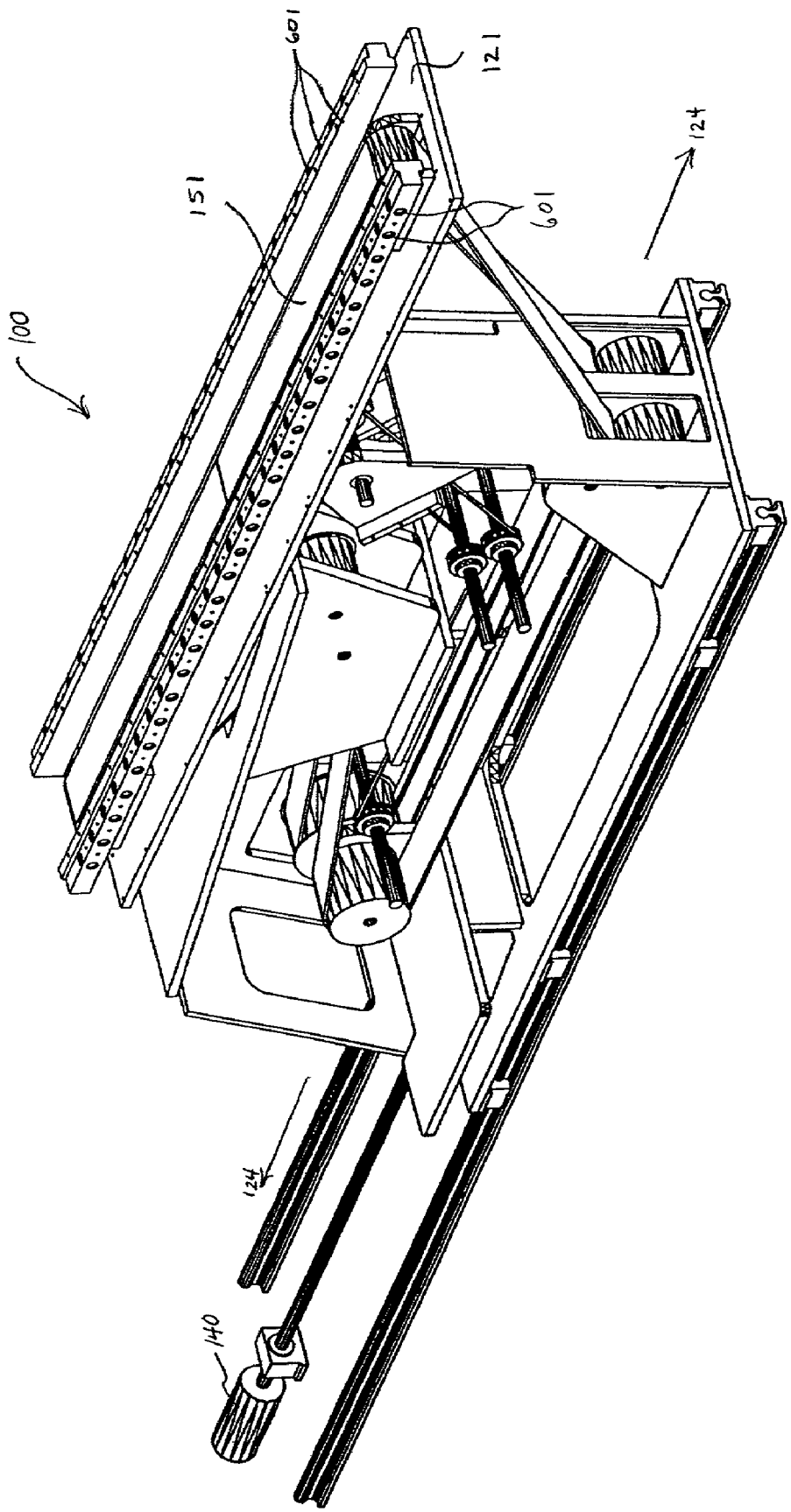
FIG. 6 shows an isometric cut-away view of portions of the positioning system of FIG. 1.

FIG. 6 shows an isometric cut-away view of portions of positioning system 100 with slab 122 removed so details of drive belt 151 can be seen. As noted above, drive belt 151 is coupled to slab 122 (not shown in FIG. 6) so that slab 122 is linearly displaceable along platform frame 121. This allows for non-horizontal, vertical, or horizontal movement of the slab depending on the rotational angle of the platform. A series of ball bearings 601 are coupled to platform frame 121 to provide smooth gliding of the slab. In one embodiment, ball bearings 601 include a ball bearing in a pack of balls.

Referring again to FIGS. 2A and 2B, in one embodiment second and third drive members 141 and 142 are regulated in coordination by a method called electronic gearing. Electronic gearing is a method which keeps the linear position of slab 122 relative to platform frame 121 the same, regardless of the rotation of the platform. This is necessary to compensate for when the platform is rotated. For instance, when platform 120 is rotated by drive member 142 via belt 152, drive member 141 must also rotate to compensate so that the belt 151 (and thus, slab 122) stays in relatively the same position it was in before. This provides that the slab will not have any linear displacement unless it is desired. In the exemplary embodiment, the electronic gearing is controlled by software running on a computer system. The exact correction needed to compensate depends on the geometry of the system. In some embodiments, the drive members can be hardwired to respond to different signals.

FIG. 7 shows a rear isometric cut-away view of portions of positioning system 100, showing a schematic representation of drive member 140 and guide member 130. Guide member 130 is attached to a floor 131 for guiding frame 110 along a second linear axis 124 generally parallel to floor 131 and perpendicular to a magnetic field axis of an MRI magnet. In the exemplary embodiment, guide member 130 is a pair of parallel rails 132A and 132B. Members 117 of frame 110 slidably mate with guide member 130 to allow frame 110 to move along secondary linear axis 124. Some embodiments include a plurality of members 117 to provide further accuracy. When used with a MRI system, movement of system 100 along the second linear axis 124 provides that the platform can be removed completely from the magnet. This facilitates loading and unloading of patients. It also helps place and locate the correct portion of the patient's anatomy within the imaging volume of the scanner. Moreover, it allows for the placement of external hardware and auxiliary fixtures such as cine fixtures, gym equipment, and so on.

Drive member 140 drives frame 110 along guide member 130. In the exemplary embodiment, drive member 140 is a screw drive motor. In one embodiment, drive member 140 includes an indexing member such as an encoder for sensing and controlling the movement of the frame along the second linear axis. For instance, driving member can be connected to a rotation counter which counts the rotations of the screw drive. In some embodiments, this information is sent to a controller such as a computer which controls and stores it. In some embodiments, drive member 140 is an encoding motor. In some embodiments, the secondary linear motion along axis 124 is provided by air or hydraulic actuation, a belt drive, a rack and pinion, or manual operation.

Figure 8A:
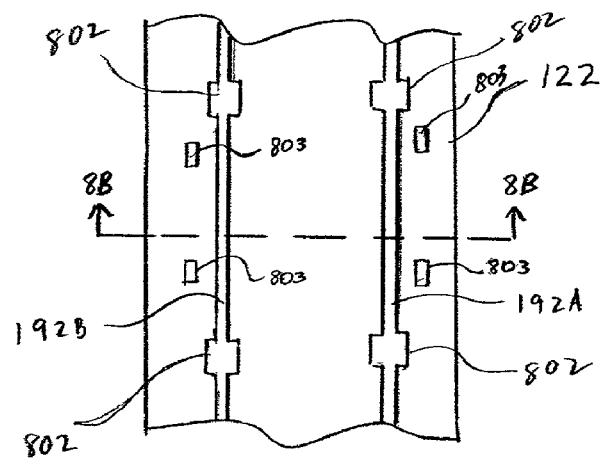
FIGS. 8A and 8B show top and side views of details of a slab of the positioning system of FIG. 1.
Figure 8B:
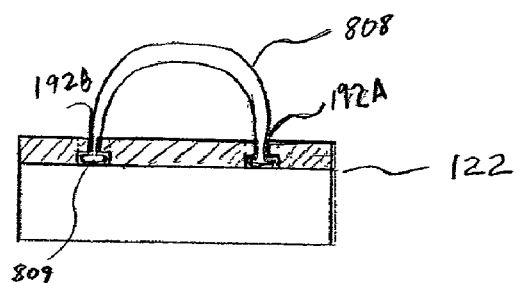

FIGS. 8A and 8B show details of slab 122 according to one embodiment. FIG. 8A shows a top view, while FIG. 8B show a cross-section of FIG. 8A. In this embodiment, slab 122 includes the pair of mounting mechanisms or connection mechanisms 192A and 192B. In one embodiment, connection mechanism 192A and 192B are dove-tailed or keyed slots. These connection members provide a location for attaching external hardware and auxiliary equipment to platform member 120. In one embodiment, each slot or mechanism 192A and 192B includes one or more notches 802 for inserting a mating portion of the auxiliary equipment. The mating portion is then slid farther down the slot to attach it to the slab. In one example, the slots run along substantially the entire surface of slab 122. Optionally, connections mechanisms 192A and 192B can include a series of discrete connection points.

FIG. 8B shows a schematic representation of a generic fixture 808 being attached to slab 122 using connection mechanisms 192A and 192B. Fixture 808 includes one or more fixture connection members 809 which are insertable through notches 802 and matingly engage with connection mechanisms 192A and 192B. By way of example, generic fixture 808 represents any external hardware or MRI fixture such as surface coils, cine fixtures, calibration equipment, patient restraints, patient seating, biopsy apparatus, patient support fixtures, stereotactic apparatus, tracking devices, exercise equipment, gymnastic equipment, robotic equipment, etc. Tracking equipment can include optical encoders, magneto-resistive encoders, position sensors, and hall probes.

In one example, surface coils are connected along the length of the slab via movable cables (not shown) located beneath the surface of slab 122. Also shown in FIG. 8A are a plurality of locating features 803. In one embodiment, locating features 803 are holes or notches which are used in place of, or in addition to, the connection mechanism 192A and 192B. Some embodiments omit one or more of connection mechanisms 192A, 192B, and/or locating features 803.

Figure 8C:
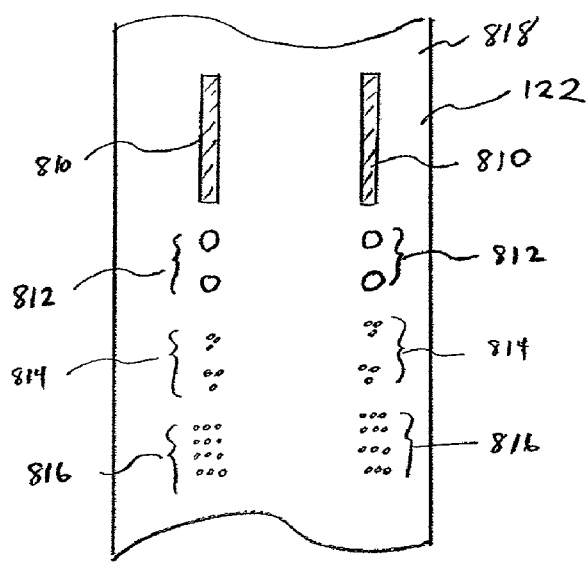
FIG. 8C shows a top view of attachment mechanisms according to one embodiment for the slab of FIG. 1.

In some embodiments, further attaching, mounting, or connection members are provided. For example, as shown in FIG. 8C, slab 122 can include one or more velcro members 810, one or more suction cups 812, one or more vacuum devices 814, a plurality of peg-board holes 816, or other equivalent attachment features and mechanisms. These attachment features are for removably mounting external hardware which has corresponding or mating attachment features. For example, the external hardware can include velcro members to removably attach the hardware to velcro members 810. In one embodiment, slab 122 can include a conveyor belt 818 having the connection members attached to its surface. This allows the connection members to be easily moved along the entire surface of the slab by running the conveyor belt in the desired direction. Among other advantages, the attachment and connection features of FIGS. 8A-8C allow the position of the external hardware to be continuously variable along most of the length of the platform.

Figure 9A:
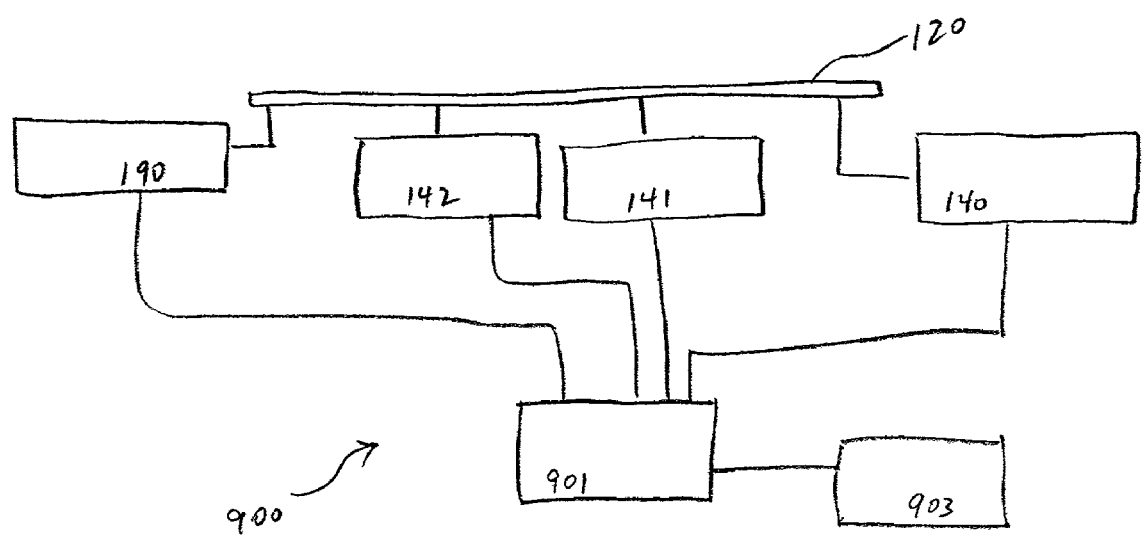
FIG. 9A shows a schematic representation of a control system according to one embodiment of the present invention.

FIG. 9A shows a schematic representation of a control system 900 according to one embodiment of the present invention. Control system 900 is for controlling the position and location of platform member 120 (relative to an MRI magnet, for instance). Platform member 120 is schematically represented. Coupled to platform member 120 are one or more sensors and/or driving members such as driving members 140-142 and positioner 190, which are also shown schematically.

Control system 900 includes a controller 901. In the exemplary embodiment, controller 901 is a computer having software for performing the controlling functions. In some embodiments, some of the controlling functions can be hard-wired into the system and/or can be performed manually. Driving members 140-142, positioner 190, and an operator input 903 are coupled to controller 901. As discussed above, in one embodiment, controller 901 performs electronic gearing to coordinate the actions of driving members 141 and 142.

Positioner 190 is a pointer which is coupled to platform 120 (see FIGS. 1 and 2). Positioner 190 is located in a slot which runs along the length of platform member 120. Positioner 190 is electrically coupled to controller 901 so that the controller knows the location of the positioner along the platform. The positioner is used by sliding the positioner to the location that is to be scanned on the patient. Thus, if a patient's chest is to be scanned, positioner 190 would be slid up the platform to the chest. If a patient's knee was to be scanned, positioner 190 would be moved to the height of the knee. Once positioned correctly, positioner 190 helps controller 901 move platform member 120 to the correct location within the MRI magnet. This is difficult to do visually and manually because the location to be scanned is typically covered with an RF coil. Thus, positioner 190 advantageously provides a precise location for scanning. Moreover, positioner 190 provides the controller with a relative location to find the correct scanning position. This is difficult to do manually because if the platform is to be tilted there is no absolute location for a user to judge distance from. In some embodiments, to be described below, a laser device is used to position a patient either vertically and/or horizontally.

In the exemplary embodiment, software on a computer controls the position of platform 120 depending on operator input at input 903 and input signals from drive members 140-142 and positioner 190 so that a patient can be positioned precisely and properly within an MRI magnet gap. In the system, the positioning is accomplished through a computer controlled motion control system. This motion control system communicates position information to the host computer for the proper execution of the scan procedure.

Input 903 can include a terminal display with keypad and switch console. The terminal is used to decide the mode the positioning system will work in and which axis is to be moved. The switch console can include one or more buttons and switches to allow the user to control the platform movement procedure. In one example, the switch console includes a rocker switch to initiate and maintain motion, a home button to return the platform to the home position, a power down button, a power up button, and an emergency shutdown button.

FIGS. 9B-9E show a flowchart representation of a method 950 for positioning the positioning system according to one embodiment of the present system.

In FIG. 9B, block 952 includes powering up the system. After powering up, the platform is calibrated in block 954. This can include setting the variables in the controller which represent the location of the platform to zero. In block 956 a patient is loaded onto the platform. In block 958, a user can choose between different modes of operation. In this example, the modes are vertical, horizontal, and tilt.

Figure 9C:
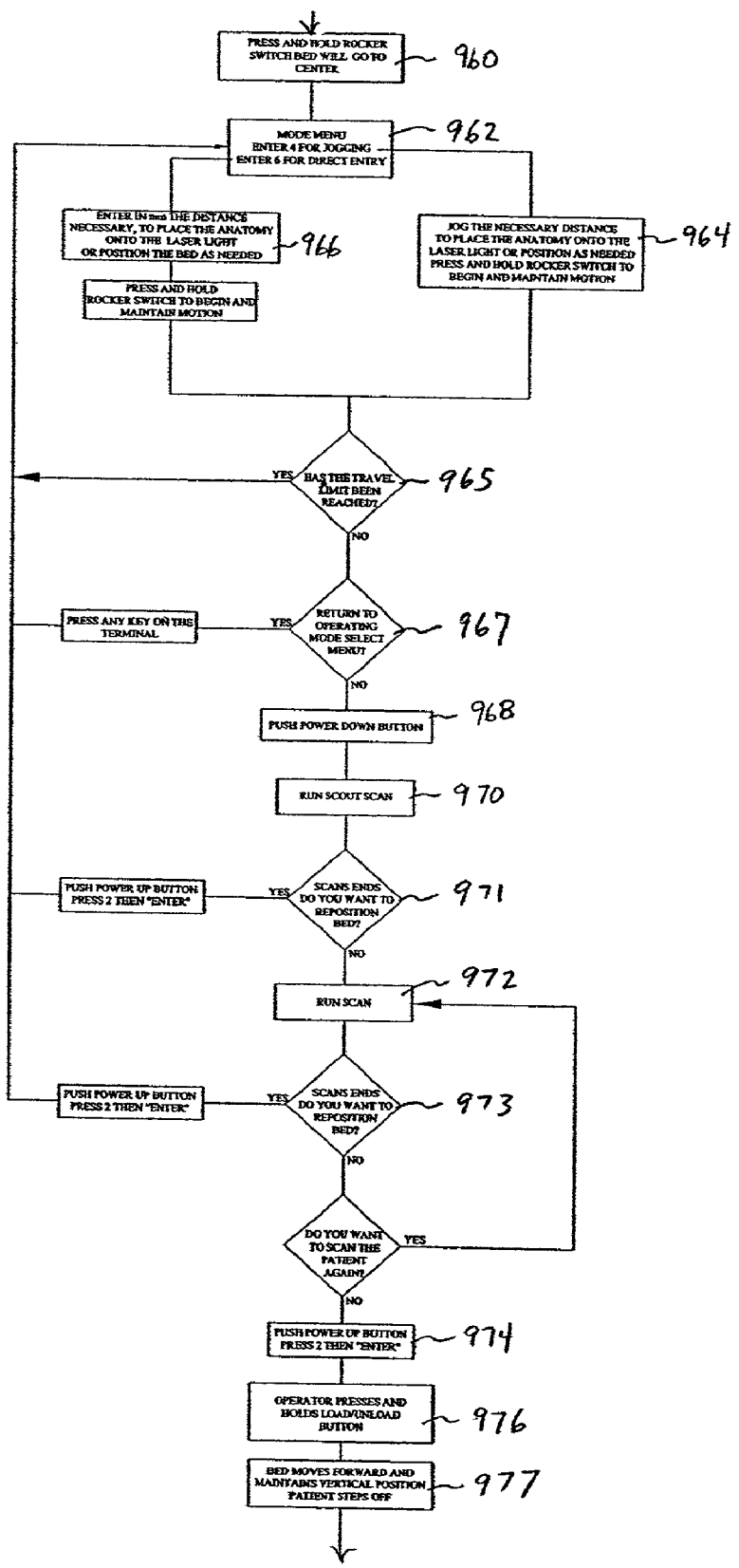

If vertical scanning is chosen, the procedure moves to block 960, as shown in FIG. 9C. Vertical scanning allows a patient to be scanned in the upright or sitting positions. In block 960 the user presses and holds the rocker switch until the display reads that the platform is centered within the magnet. Then in block 962, the user has a choice between jogging or direct entry. If jogging is chosen, the method goes to block 964. Jogging allows the user to move the patient up and down by manually pressing and holding the rocker switch. As the platform is being jogged, the display can show how far the platform has been moved.

Referring to block 965, it is noted that if the travel limit of the platform is reached during jogging mode or direct entry mode, the platform will automatically stop moving, the display will read that the travel limit has been reached, and the method will return to block 962.

If direct entry is chosen in block 962, then the method goes to block 966, where the user enters the distance they want the platform to move in millimeters, or other units if so desired. The rocker switch is then held down until the platform moves that desired distance.

In one embodiment, a laser can be used to help position the patient. The laser is positioned a known distance from the center of the magnet. Thus, the user moves the platform until the relevant portion of the anatomy is highlighted by the laser. Then the platform can be centered so that the laser highlighted portion of the anatomy is centered within the magnet. Typically, when used for vertical positioning, the laser would only function as a visual reference.

After the platform has been satisfactorily positioned, the platform can be powered down in block 968, and the MRI scanning process begins.

Before, between, and after each of the scout scan and regular scans in blocks 970 and 972, the user is given a choice of powering up the system and repositioning the patient in blocks 967, 971, and 973.

Once the scan is competed the system is powered up in block 974. If the patient is done being scanned, the user presses and holds the unload or home button in block 976 and the platform moves forward in the vertical position to the unload position, where the patient steps off, denoted in block 977.

Referring again to FIG. 9B, if in block 958 the user chooses horizontal movement, the method goes to block 978, as shown in FIG. 9D. Here, the user presses and holds the rocker switch and the platform rotates until the platform is horizontal. Then in block 980, the user is given a choice between jogging, direct entry or centering.

Centering is used when the anatomy to be scanned is highlighted by a laser. Again, this is typically done by using jogging in block 981 and/or direct entry in block 983 until the portion of the anatomy is highlighted by the laser. When centering is then chosen, the rocker switch is held down and the platform will be positioned so that the laser highlighted portion of the anatomy is in the center of the magnet gap, as shown in block 982.

The method then goes through a series of positioning, scanning, and unloading steps similar to those described above for vertical scanning. In FIG. 9D like numbers have been used to denote similar blocks of the vertical procedure described for FIG. 9C, and the methods will not be described here in detail. At the end of the scan procedure, in block 984 the platform is rotated to the vertical position and the patient steps off.

Figure 9E:
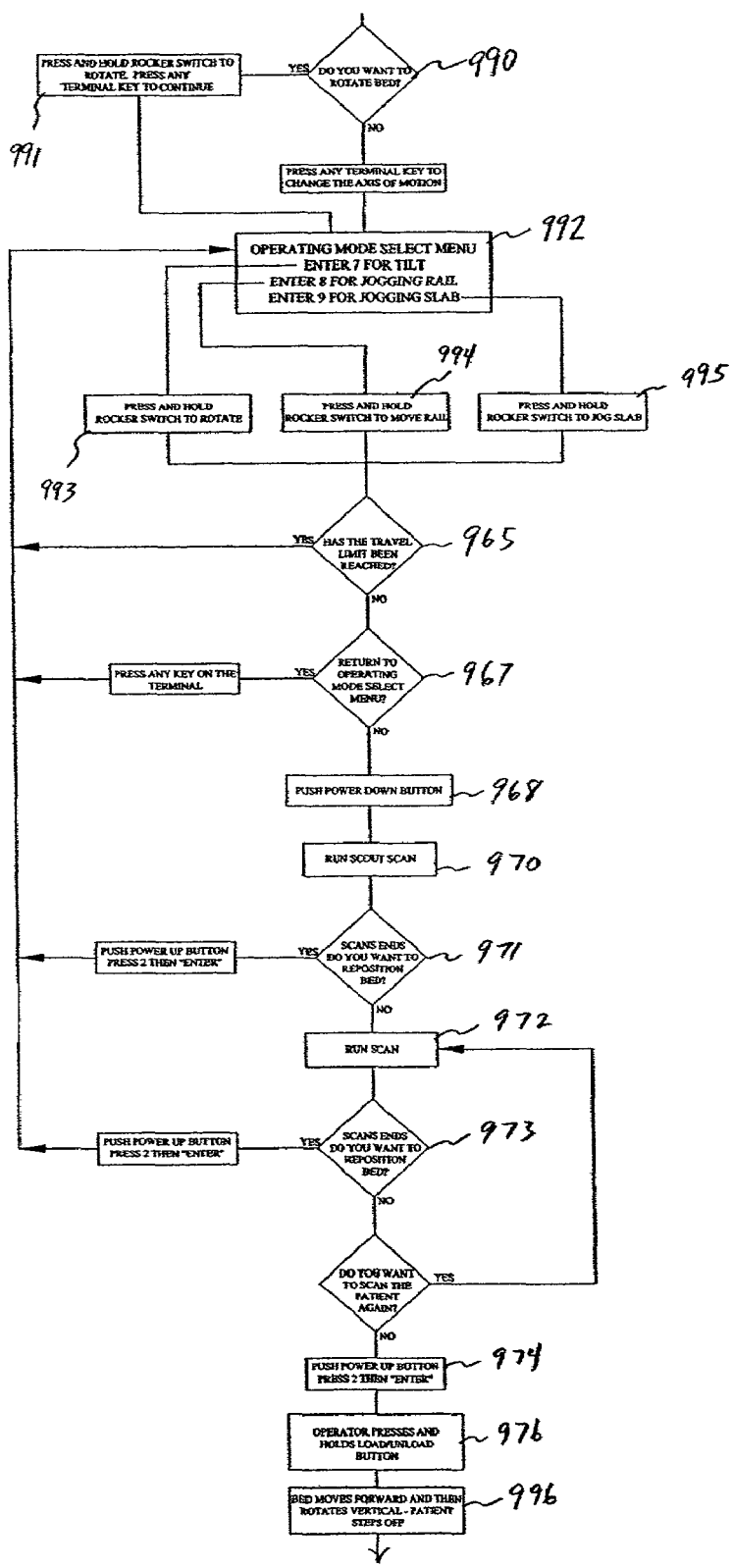

Referring again to FIG. 9B, if in block 958, the user chooses tilt mode, the method goes to block 990, as shown in FIG. 9E. From block 990, the user can choose to rotate the platform in block 991 or to go to another menu in block 992. In block 992, the user is given a choice to tilt, jog on the floor guide, or jog on the slab.

If rotating is chosen, the method goes to block 993, where the rocker switch is held as the platform rotates and the terminal displays the platform angle. When the slab is extended (i.e. not centered), the platform can rotate from vertical to 0 degrees (horizontal). The present system allows the slab to be extended half the total possible excursion when rotated at angles between 30 degrees and 45 degrees; and slab extension for the total possible excursion is possible from 30 degrees to 0 degrees. Thus, the possible rotation angle of the slab is a function of the degree of extension of the slab, and conversely, the possible degree of slab extension is dependent on the rotation angle of the slab. Although this describes one implementation of the logical control of the platform slab motion, the inherent capabilities of the motion control of the slab are not limited to the conditions described herein. As will be described below, when in tilt mode and when the platform is being jogged, the system displays when the slab is centered. In one embodiment, the system emits audible beeps which indicate that the slab is centered.

If jog on the rail is chosen, then in block 994 the user can hold the rocker switch to move the platform along the rails while the display shows the amount of travel. Again, whenever the platform reaches any travels limits, it is automatically stopped by the system. When the platform is vertical and the user is jogging horizontally, the system will display when the platform is over the access hole (See FIG. 10A), at which time the user will know the platform can safely be moved up and down vertically.

If jogging the slab is chosen, the method goes to block 995. Here, the user can hold the rocker switch to move the platform while the display shows the slab position. As noted above, as the slab moves through the center position, the terminal displays the center position. If the platform is vertical and over the access hole the user can jog the slab member up and down and if the platform is rotated beyond 45 degrees the user can jog the slab. These jogging constraints help assure that the platform will stay in the envelope of the magnet frame.

The method then goes through a series of positioning, scanning, and unloading steps similar to those described above for vertical scanning. In FIG. 9E like numbers have been used to denote similar blocks of the vertical procedure described for FIG. 9C, and the methods will not be described here in detail. At the end of the scan procedure, in block 996 the platform rotates to the vertical position and the patient steps off.

FIGS. 10A-15 show one example of positioning system 100 being used for positioning a patient within an MRI system. In the exemplary embodiment, platform member 120 has a width which allows it to fit within an MRI magnet gap.

Figure 10A:
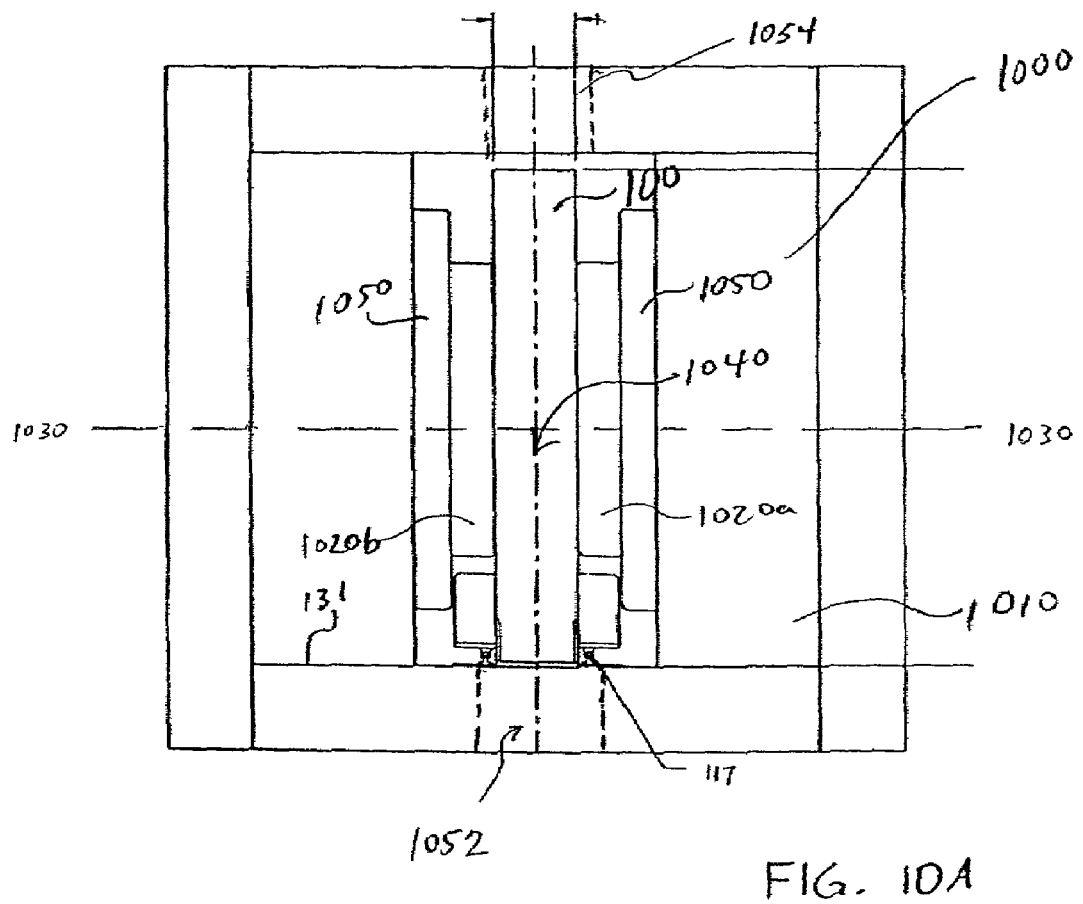
FIG. 10A shows the positioning system of FIG. 1 located within an MRI magnet in accordance with one embodiment.

FIG. 10A shows a front view of an exemplary MRI magnet 1000 with positioning system 100 located therein. Magnet 1000 includes a pair of opposed poles 1020A and 1020B projecting towards one another along a horizontally oriented magnetic field axis 1030, and defining a patient receiving space or gap 1040. In one embodiment, flux generating means such as permanent magnets associated with a frame 1010, superconducting coils encircling portions of the frame, or resistive electrical coils 1050 encircling portions of frame 1010 are provided. In one embodiment, an iron core magnet is utilized. In one embodiment, magnetic field axis 1030 is approximately 5-6 feet (about 1.5-2.0 meters) above floor 131 so that the head of a standing adult can be positioned at or near the magnetic field axis. The exemplary system of FIG. 10A includes a hole 1052 covered by an access door or false floor. A second hole 1054 is located above the scanning area of the magnet. This allows the platform of system 100 to be raised into the hole. Details of the use of hole 1052 will be discussed below.

Figure 10B:
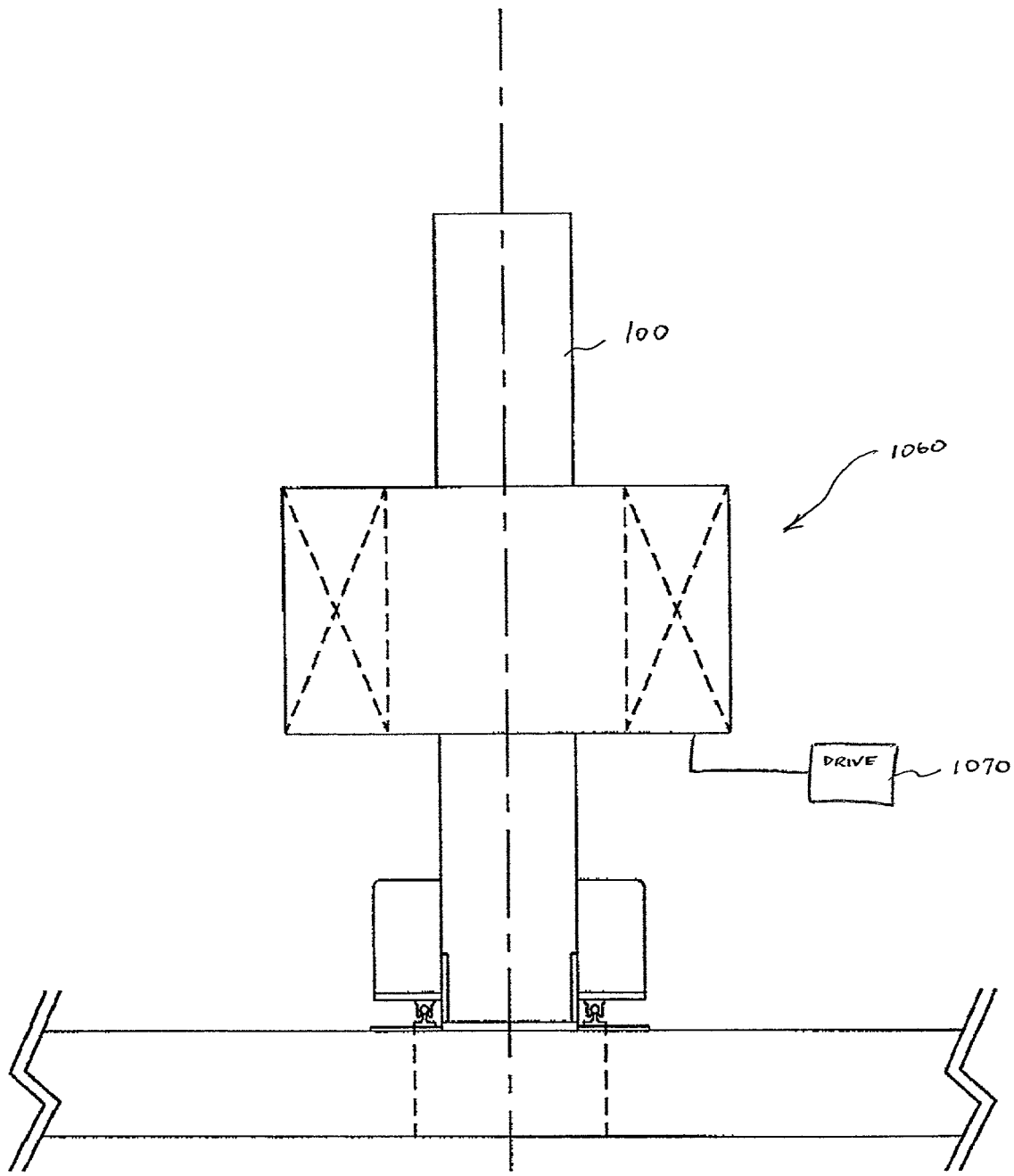
FIG. 10B shows the positioning system of FIG. 1 located within an MRI magnet in accordance with one embodiment.

FIG. 10B shows a front view of an MRI magnet 1060 with positioning system 100 located therein. Magnet 1060 is a solenoidal shaped magnet having a central hole and a magnetic axis which runs in a vertical direction. In this example, positioning system 100 is placed inside the central hole so that the magnetic axis of magnet 1060 is collinear with the platform vertical axis.

In one embodiment, magnet 1060 can have wall, ceiling, and/or floor mounted supports which include a drive 1070, such as a motor, a gearing system or other drive system for translating the magnet up and down in a vertical direction.

Accordingly, this provides a system for moving magnet 1060 in addition to, or instead of, moving positioning system 100. For example, a patient can be loaded on the platform and positioning system 100 moved vertically as described above.

Then, magnet 1060 can be moved vertically relative to the platform. Some embodiments can include supports for magnet 1060 allowing the magnet to be rotated. In one embodiment, magnet 1060 is a superconducting magnet.

FIGS. 11-15 show side views of various positions of positioning system 100 within MRI magnet 1000. In FIGS. 11-15, drive belts 151 and 152 are not shown for reasons of clarity. A belt 1111 is shown which loops around various idler pulleys and around the shaft of rotational axis 112. In various embodiments, belt 1111 provides tension on axis 112 and/or sensing and feedback to a controller for sensing the position of platform 120.

Figure 11A:
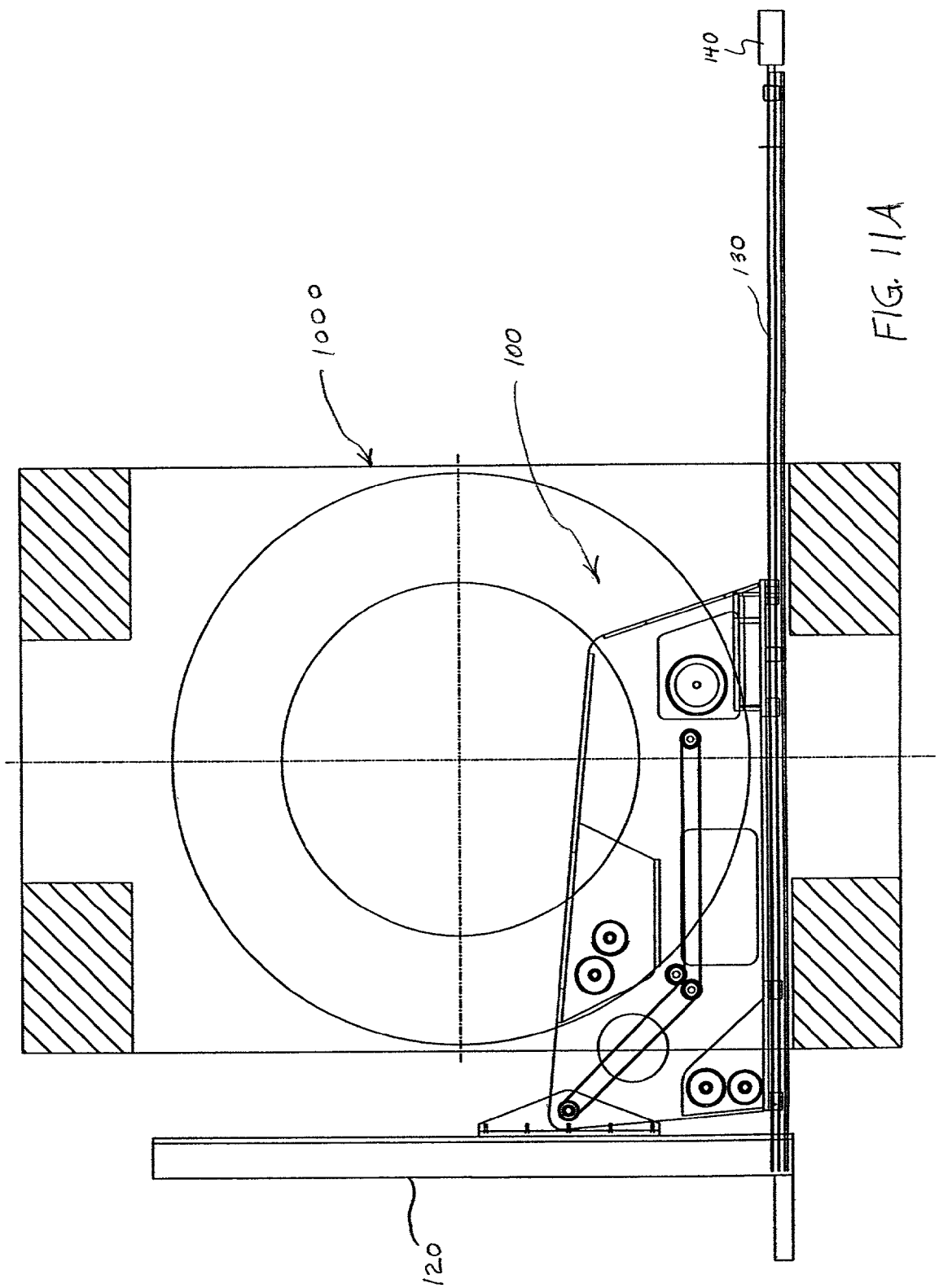
FIG. 11A shows a side view of the positioning system of FIG. 1 located within an exemplary MRI magnet.

FIG. 11A shows system 100 located outside of the magnet gap with platform 120 in an initial position comprising a generally vertical orientation. This is the position the system will typically be used to load a patient. In the exemplary embodiment, the initial position is as shown in FIG. 11A. In one embodiment, the initial position is slightly past the vertical orientation (tilted backwards) so that the patient feels more secure. Either before or after the patient gets on the platform, any RF coils, pads, cine fixtures, or other needed external hardware components can be attached to the connection mechanisms and RF connectors on the platform, and positioner 190 (not shown) can be correctly positioned to point at the pertinent anatomy. The operator then enters the necessary scanning location information into a controller such as a computer, which may be located nearby the magnet or in another room from the system. The operator may enter information such as whether the scan is to be horizontal, vertical or a tilt scan, as described above regarding FIGS. 9A and 9B-9E.

FIG. 11B shows the same view as FIG. 11A, with the addition of a removable seat 1101. Removable seat 1101 is removably attachable to platform 120 using notches, holes, or attachment mechanisms on the platform with mating attachment members on the seat. FIG. 11B shows an exemplary patient 1102 seated on seat 1101. In some embodiments, FIGS. 12-15, which follow, can also incorporate a seat such as seat 1101. Moreover, as noted above, various other devices, such as RF coils, patient restraints, or shoulder pads, for example, can be attached to platform 120.

Figure 12:
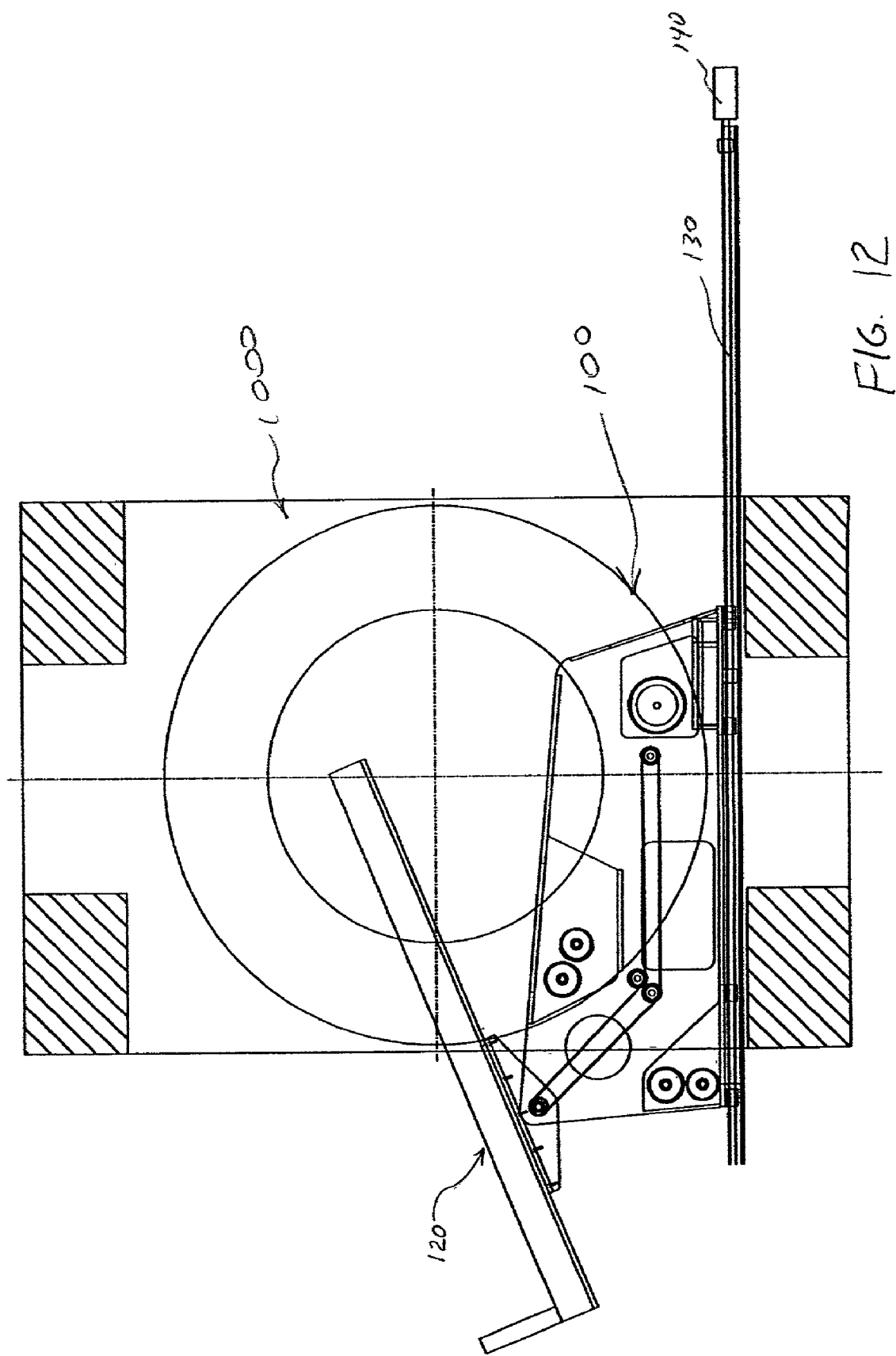
FIG. 12 shows another side view of the positioning system of FIG. 1 located within an exemplary MRI magnet.

FIG. 12 shows system 100 as platform 120 is being rotated. In some embodiments, this is the final angle of the platform, and the system is driven along guide members 130 into the magnet gap. Alternatively, the platform can be rotated to any of a variety of positions.

Figure 13:
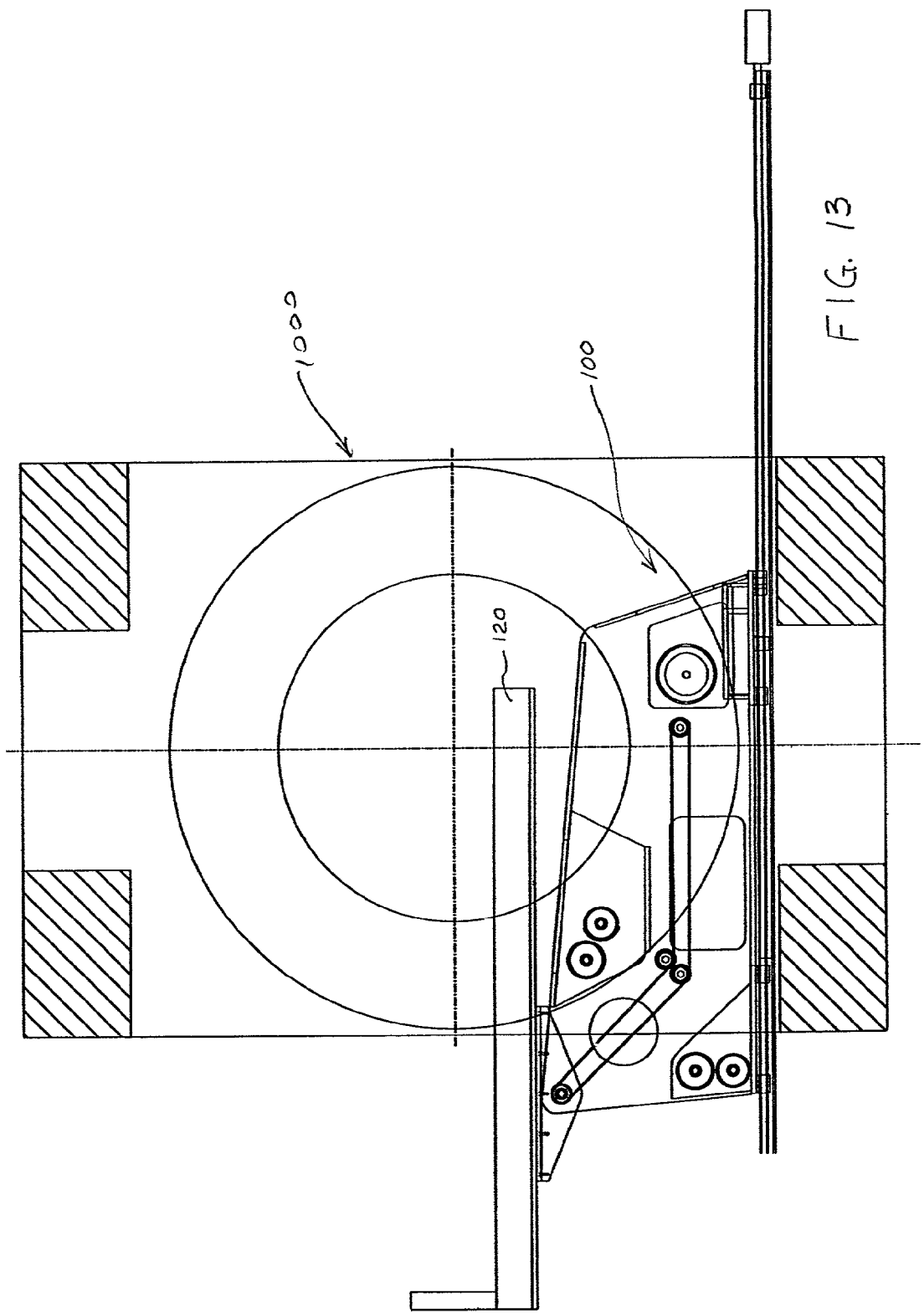
FIG. 13 shows another side view of the positioning system of FIG. 1 located within an exemplary MRI magnet.

FIG. 13 shows platform 120 in a horizontal position. Some embodiments rotate the platform even further into a Trendelenburg position. In one method of operation, a laser is activated and the platform is moved by the operator until the laser is located on the anatomy to be scanned. As described above for FIGS. 9B-9E, once the laser is lined up, the operator activates the system and the platform is automatically moved so that the portion of the anatomy where the laser was pointing is in center of the magnetic field. A scout or test scan is run, the operator offsets the platform slab if necessary and the scan is then performed.

In other embodiments, as discussed above, the controller automates the positioning process using the positioner 190 and the drive members.

Figure 14:
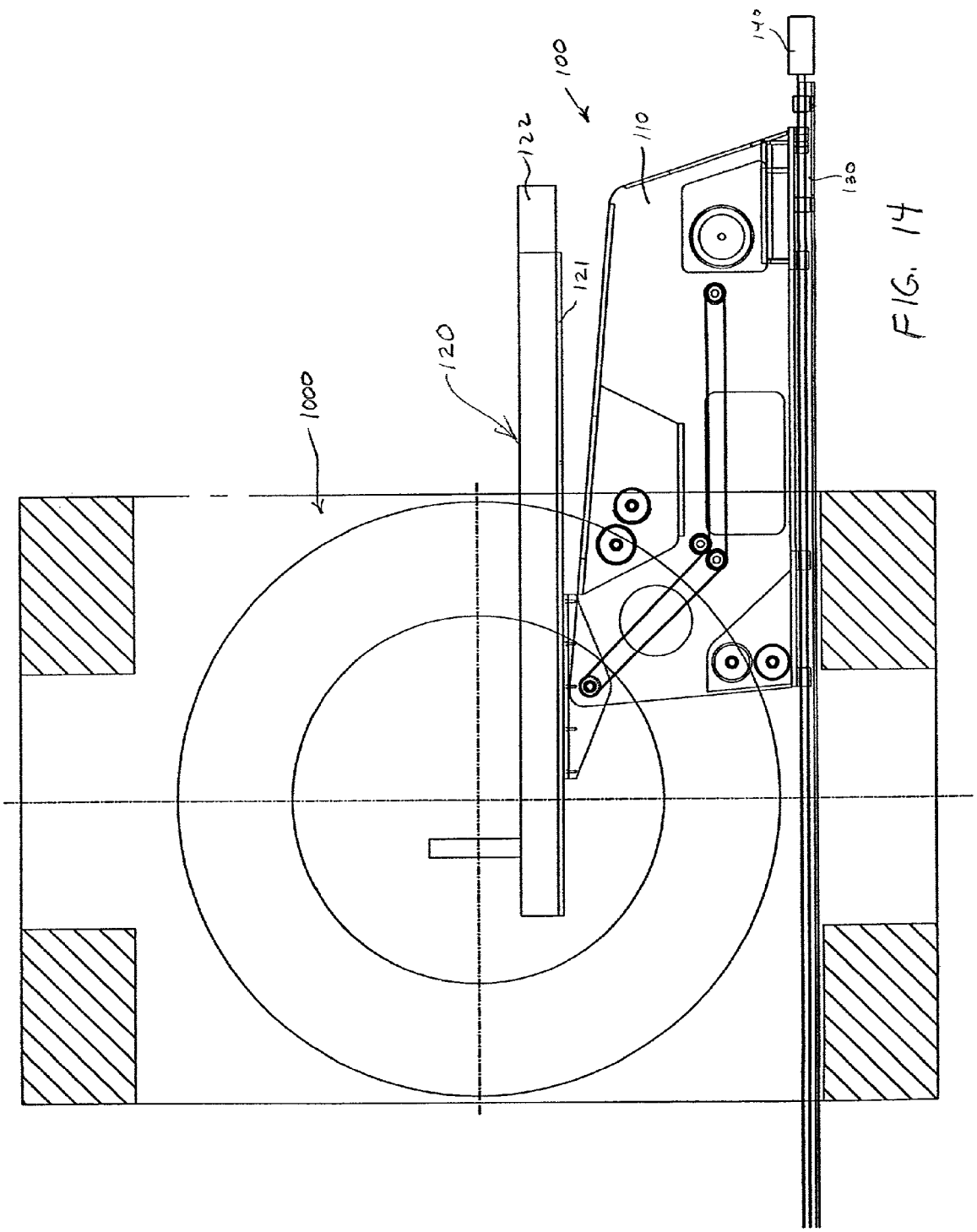
FIG. 14 shows another side view of the positioning system of FIG. 1 located within an exemplary MRI magnet.

In FIG. 14, frame 110 has been driven back along guide members 130 and slab 122 has been linearly moved along platform frame 121 into an exemplary scanning position. If necessary, the operator fine-tunes the position of the patient manually. For instance, the computer can contain an input allowing for movements as small as a millimeter at a time. Advantageously, the rotation counters of the exemplary driving members can provide such accuracy.

In FIG. 15, slab 122 of platform 120 is lowered into hole 1052. This permits scanning of portions of the body which are higher up (neck and head, for example) while the patient is in a vertical orientation. In the exemplary embodiment, a false floor is located over hole 1052. The false floor is separately motorized and connected to the controller of the system and only opens when the system is going to be used in a position as shown in FIG. 15 and only when the system is in position for it to be lowered. This ensures that nothing will accidentally fall into the hole. Again, hole 1054 located above the scanning area can also be used for receiving a portion of the platform when the platform needs to be raised above the height of the magnets during a scanning procedure.

When the MRI scan is done, the platform is moved to an unloading position, such as the initial position of FIG. 11, and the patient is unloaded.

Among other advantages, the ability to accurately position a patient in a variety of orientations allows scanning the patient in essentially any posture. This improves the realism of the scanned image and allows detection of posture dependent problems. For example, a patient having difficulties with a knee joint can be imaged while the joint is bearing weight, with the patient in a standing position. Also, internal organs can be brought to the positions which they occupy when the patient is standing or seated. Moreover, since in one embodiment, the present system senses the position of the platform via positioner 190 and the motor rotation counters or other sensors, a scan of a patient in an non-standard position can be coordinated by software and the correct axes can be labeled for any given scan.

The present system is suitable for use in screening studies as well as the usual studies carried out by magnetic resonance. Additionally, it provides for MRI studies of the upright or angled patient where the studies can be performed while the human body, spine, joints, nervous central system, and other organs are acted upon by the gravitational field, loading it as it normally loads the upright human body.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A magnetic resonance imaging system comprising:
   (a) a magnet having a pair of opposed pole elements defining a field axis and a patient-receiving space between said pole elements;
   (b) one or more guide members extending horizontally along a guide axis transverse to said field axis;
   (c) a carriage frame movable relative to said magnet along said guide members, said frame defining a pivot axis substantially parallel to said field axis;
   (d) a patient support defining a support direction transverse to said pivot axis, said patient support and said support direction being pivotable through a range of orientations relative to said carriage frame about said pivot axis, the patient support being linearly movable relative to said pivot axis and relative to said carriage frame in said support direction separately from pivoting motion of the patient support about said pivot axis when said support and said support direction are in any orientation within said range;
   (e) one or more drive mechanisms adapted to actuate said pivoting movement and support direction movement of said support and movement of said frame along said one or more guide members; and (f) a controller connected to said one or more drive mechanisms and operative to command said one or more drive mechanisms to move said support from a loading position to an imaging position in which at least a portion of said patient support is disposed within said imaging space.

2. The system of claim 1, wherein the patient support has one or more connection mechanisms for removably attaching one or more MRI fixtures to the patient support.

3. The system of claim 2, wherein the connection mechanism is adapted to mount said MRI fixture at substantially any location along the patient support.

4. The system of claim 2, further comprising a foot-stand extending generally perpendicular relative to a major surface of the patient support.

5. The system of claim 2, wherein the patient support includes attachment members for removably mounting a seat to the patient support.

6. The system of claim 2, further comprising supports which are removably attachable to the patient support, the supports being adapted for cushioning a patient's shoulders.

7. The system of claim 2, further comprising one or more RF connection ports mounted to the patient support, the system further comprising an RF receiver and a circuit arranged to connect one or more of said RF connection ports to said receiver.

8. The system of claim 2, wherein the patient support includes a form fitting mattress material.

9. The system of claim 2, wherein the one or more connection mechanisms includes a dove-tailed slot located on the patient support.

10. The system of claim 2, wherein the one or more connection mechanisms includes a member chosen from a group consisting of hook-and-loop fasteners, suction cups, and vacuum devices.

11. The system of claim 2 further comprising a conveyor belt which is movably attached to said patient support, said one or more connection mechanisms including a mounting mechanism attached to said conveyor belt.

12. The system of claim 2, further comprising one or more MRI fixtures adapted to engage said one or more connection mechanisms.

13. The system of claim 12, wherein the one or more MRI fixtures includes one or more fixtures for use in performing MRI scans of specific anatomic regions of the patient.

14. The system of claim 12, wherein the one or more MRI fixtures includes one or more RF coils.

15. The system of claim 12, wherein the one or more MRI fixtures includes a member chosen from a group consisting of surface coils, cine fixtures, calibration equipment, patient restraints, patient seating, biopsy apparatus, patient support fixtures, stereotactic apparatus, tracking devices, exercise equipment, gymnastic equipment, and robotic equipment.

16. The system of claim 1 wherein said pivot axis is substantially horizontal.

17. The system of claim 16 wherein said one or more guide members extend below said pivot axis.

18. The system of claim 1 wherein said controller is operative to command said one or more drive mechanisms to bring said patient support to any one of a plurality of imaging positions.

19. The system of claim 1 wherein said patient support includes an elongated platform extending in said support direction.

20. The system of claim 19 wherein, when said patient support is in said loading position, said elongated platform extends generally vertically.

21. The system of claim 20 wherein, when said patient support is in said loading position, faces in a forward direction away from said field axis, and movement of the patient support from said loading position to said imaging position includes movement of said frame in a rearward direction along said one or more guide members.

22. The system of claim 21 wherein, when said patient support is in said loading position, said patient support is disposed outside of said magnet but adjacent thereto.

23. The system of claim 20 wherein said patient support includes a foot rest and said foot rest is disposed near the bottom of the platform when said support is in said loading position.

24. A method of positioning a patient for magnetic resonance imaging comprising the steps of:

(a) loading a patient on a patient support while the patient support is disposed in a loading position with the support in proximity to a magnet;

(b) specifying an imaging position for the patient support; and (c) moving the patient support from said loading position to said imaging position by:
  (i) rotating the patient support about a pivot axis parallel to the field axis;
  (ii) moving the patient support linearly relative to the pivot axis in a support direction transverse to the pivot axis, the linear movement of the patient support being performed separately from rotation of the patient support about the pivot axis; and
  (iii) moving the pivot axis linearly along a horizontal guide axis transverse to the field axis.

25. The method as claimed in claim 24 wherein said patient support is pivotably mounted to a carriage frame defining said pivot axis and said step of moving the pivot axis includes moving the frame relative to the magnet.

26. The method as claimed in claim 25 wherein said step of moving the carriage frame includes moving the carriage frame on one or more guide members extending along said guide axis.

27. The method as claimed in claim 24 wherein said patient support includes an elongated platform and, when said patient support is in said loading position, said elongated platform extends generally vertically.

28. The method as claimed in claim 27 wherein said patient support includes a foot rest projecting from said elongated platform, and said foot rest is disposed near the bottom of the elongated platform when the patient support is in said loading position.

29. The method as claimed in claim 27 wherein said platform faces in a forward direction when said patient support is in said loading position and said step of moving said pivot axis includes moving said pivot axis along said guide axis in a rearward direction, opposite to said forward direction.

30. The method as claimed in claim 24 wherein, when said patient support is in said loading position, said patient support is disposed outside of said magnet but adjacent thereto.

* * * * *